United States Patent
Andersen et al.

(10) Patent No.: US 11,759,623 B2
(45) Date of Patent: Sep. 19, 2023

(54) IMPLANTABLE MEDICAL DEVICES INCLUDING LOW FREQUENCY AND HIGH FREQUENCY CLOCKS AND RELATED METHODS

(71) Applicant: Pacesetter, Inc., Sylmar, CA (US)

(72) Inventors: Dean Andersen, San Jose, CA (US); Eiji Shirai, Mountain View, CA (US)

(73) Assignee: Pacesetter, Inc., Sylmar, CA (US)

( * ) Notice: Subject to any disclaimer, the term of this patent is extended or adjusted under 35 U.S.C. 154(b) by 224 days.

(21) Appl. No.: 17/081,114

(22) Filed: Oct. 27, 2020

(65) Prior Publication Data

US 2021/0205604 A1    Jul. 8, 2021

Related U.S. Application Data

(60) Provisional application No. 62/958,132, filed on Jan. 7, 2020.

(51) Int. Cl.
*A61B 17/00* (2006.01)
*A61N 1/02* (2006.01)
(Continued)

(52) U.S. Cl.
CPC .............. *A61N 1/025* (2013.01); *A61N 1/362* (2013.01); *A61N 1/3756* (2013.01);
(Continued)

(58) Field of Classification Search
CPC ................................ A61N 1/362; A61N 1/025
(Continued)

(56) References Cited

U.S. PATENT DOCUMENTS 6,681,192 B2    1/2004    Ballantyne
7,047,433 B2    5/2006    Lin
(Continued)

FOREIGN PATENT DOCUMENTS

WO    WO-2014047205 A1 *    3/2014    ............. G01D 21/00
WO    WO2019/138102 A1    7/2019

OTHER PUBLICATIONS

International Search Report & The Written Opinion of the International Searching Authority dated Apr. 9, 2021, International Application No. PCT/US2021/012088.

*Primary Examiner* — Nicole F Lavert
*Assistant Examiner* — Nicole F Johnson
(74) *Attorney, Agent, or Firm* — Vierra Magen Marcus LLP

(57) ABSTRACT

Techniques for calibrating a low frequency (LF) clock of an IMD are disclosed, wherein the IMD also includes a high frequency (HF) clock. This includes determining an average, or a surrogate thereof, of how many HF clock cycles of a HF clock signal (produced by the HF clock) occur per LF clock cycle of a predetermined number N of LF clock cycles of the LF clock signal (produced by the LF clock), wherein N is an integer that is at least 2. This also includes comparing the average or a surrogate thereof to a corresponding target value that the average or the surrogate thereof would be equal to if the frequency of the LF clock signal equaled a target frequency for the LF clock, wherein the corresponding target value need not be an integer. The LF clock is calibrated by adjusting the frequency thereof based on results of the comparing.

25 Claims, 7 Drawing Sheets

(51) Int. Cl.
    *A61N 1/372* (2006.01)
    *A61N 1/362* (2006.01)
    *G16H 40/63* (2018.01)
    *A61N 1/39* (2006.01)
    *G06F 1/08* (2006.01)
    *G16H 20/30* (2018.01)
    *A61N 1/375* (2006.01)

(52) U.S. Cl.
    CPC ....... *A61N 1/37276* (2013.01); *A61N 1/3956* (2013.01); *G06F 1/08* (2013.01); *G16H 20/30* (2018.01); *G16H 40/63* (2018.01)

(58) Field of Classification Search
    USPC ............................................................ 607/5
    See application file for complete search history.

(56) References Cited

U.S. PATENT DOCUMENTS

| | | |
|---|---|---|
| 8,805,505 B1 | 8/2014 | Roberts |
| 8,825,170 B2 | 9/2014 | Bond et al. |
| 9,079,040 B2 | 7/2015 | Bond et al. |
| 2005/0103351 A1 | 5/2005 | Stomberg |
| 2006/0184213 A1* | 8/2006 | Griffith ................ A61N 1/3727 607/57 |
| 2014/0210524 A1* | 7/2014 | Roberts .................... H03L 7/24 327/144 |
| 2019/0076663 A1* | 3/2019 | Andersen ........... A61N 1/36167 |

* cited by examiner

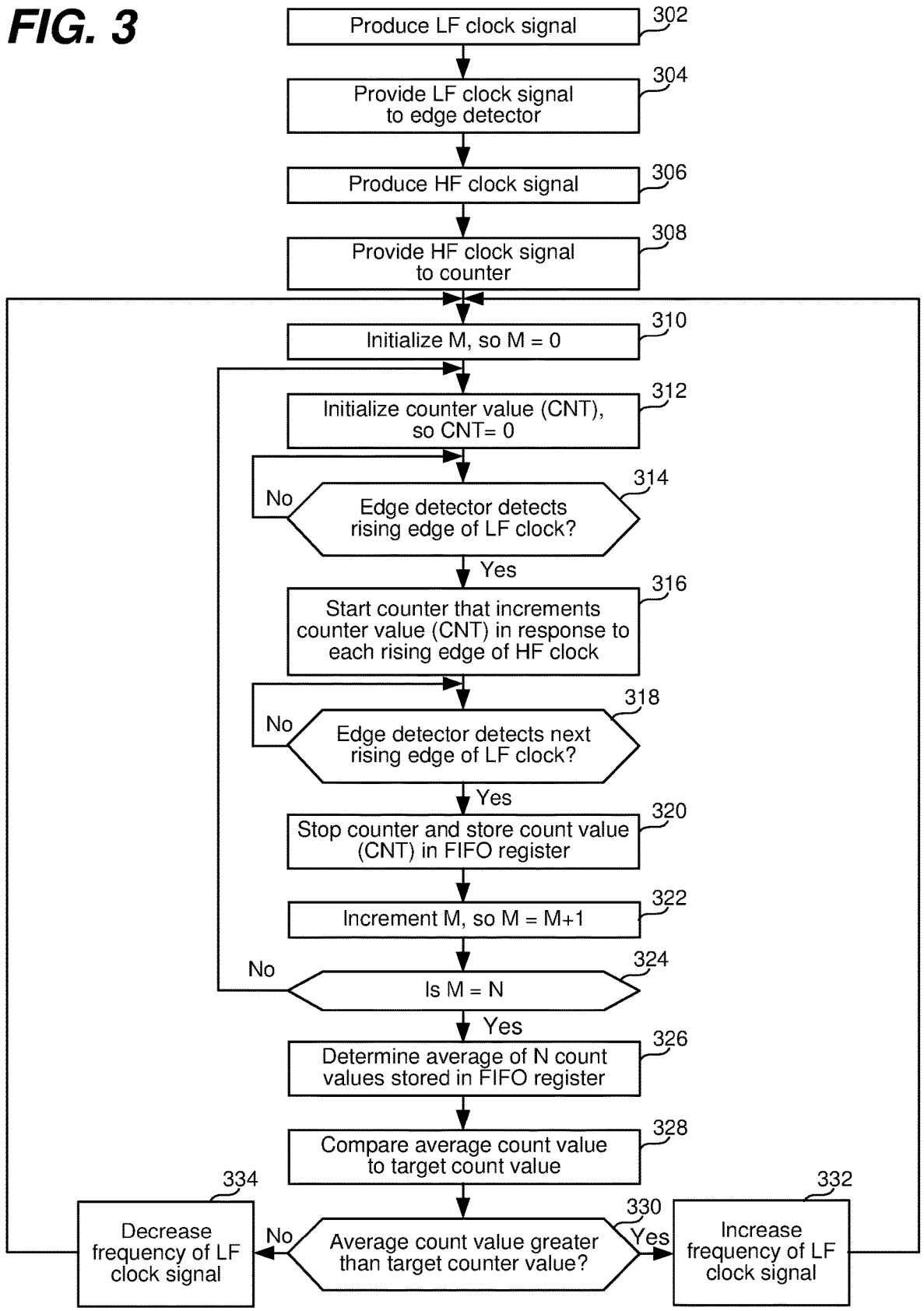

IMPLANTABLE MEDICAL DEVICES INCLUDING LOW FREQUENCY AND HIGH FREQUENCY CLOCKS AND RELATED METHODS

PRIORITY CLAIM

This application claims priority to U.S. Provisional Patent Application No. 62/958,132, filed Jan. 7, 2020, which is incorporated herein by reference in its entirety.

FIELD OF TECHNOLOGY

Embodiments of the present technology generally relate to implantable medical devices and timing sources (aka clocks) thereof that can be used for radio frequency communications as well as to provide therapy and/or sensing capabilities.

BACKGROUND

Implantable medical devices (IMDs), such as traditional pacemakers, leadless cardiac pacemakers (LCPs), implantable cardioverter-defibrillators (ICDs), neurostimulators, and pulmonary artery pressure (PAP) sensors, just to name a few, typically need a timing source (also referred to a clock generator or a clock) to perform therapy and/or sensing at appropriate times. Such therapy can include delivering pacing pulses, neurostimulation pulses, defibrillation shocks, and/or the like. Such sensing can include sampling of one or more sensed signals, such as an intracardiac electrograms (IEGM), cardiogenic impedance signal, photoplethysmography (PPG) signal, PAP signal, and/or the like.

The traditional timing source for an IMD includes a crystal oscillator, which can also be referred to more succinctly herein as a crystal. Typical crystal oscillators, known as watch crystals, may run at 32.768 kHz, or even higher frequencies of 100-500 kHz. Beneficially, relatively low frequency crystal oscillators can be designed for very low power operation and low drift over time. However, a drawback to relatively low frequency crystal oscillators is that they may be larger than desired, since the size of a crystal oscillator is typically inversely proportional to the frequency of the oscillator. For certain types of IMDs, such as LCPs and PAP sensors, size is a big constraint. Another drawback to crystal oscillators is that they are typically more expensive than non-crystal timing sources. Further, where a high frequency timing signal (also referred to as a HF clock signal) is needed, e.g., for providing radio frequency (RF) communication capabilities, high frequency crystal oscillators used to produce such HF clock signals may consume more power than desired, because the power consumed by a crystal oscillator is typically proportional to the squared-_frequency of the oscillator. In other words, in general the higher the frequency of a crystal oscillator, the more power consumed by the crystal oscillator.

Many IMDs use radio frequency (RF) technology for communications. Whether the technology used is BLE (Bluetooth Low Energy) or MICS (Medical Implant Communication System), RF-based communication protocols require crystal oscillators to pass compliance testing. The reason crystals are needed is because compliance testing requires that radios (also known as transceivers) of IMDs have stable frequencies over time and temperature. In general, the clock frequencies needed for RF communication subsystems are much higher than the ones used by IMDs to provide therapy and/or sensing at appropriate times. For example, clock frequencies needed for RF communication subsystems are typically in the range of 30-50 MHz, while clock frequencies needed to provide therapy and/or sensing at appropriate times are typically many orders of magnitude lower, e.g., in the range of 30-500 kHz.

Many IMDs have two timing sources, including a first timing source that is used for RF communications, and a second timing source that is used to perform therapy and/or sensing at appropriate times, wherein the first timing source operates at a higher frequency than the second timing source, and thus, the first timing source consumes more power than the second timing source when turned on (aka enabled). The timing source that is used for RF communications can also be referred to more specifically herein as an RF timing source, and the timing source that is used for controlling the timing of therapy and/or sensing can also be referred to more specifically herein as a system timing source. In order to conserve energy, the RF timing source (that is used for RF communications) may be disabled when it is not being used. By contrast, the system timing source (that is used to provide therapy and/or sensing at appropriate times) is typically continuously enabled.

SUMMARY

Certain embodiments of the present technology related to methods for use with an implantable medical device (IMD) that includes a low frequency clock and a high frequency clock, wherein the high frequency clock when enabled consumes more power than the low frequency clock. Such a method includes the low frequency clock producing a low frequency clock signal, and the high frequency clock producing a high frequency clock signal having a frequency that is at least an order of magnitude greater than a frequency of the low frequency clock signal. The method also includes determining an average, or a surrogate thereof, of how many high frequency clock cycles of the high frequency clock signal occur per low frequency clock cycle of a predetermined number N of low frequency clock cycles of the low frequency clock signal, wherein the predetermined number N is an integer that is at least 2. The method also includes comparing the average or a surrogate thereof to a corresponding target value that the average or the surrogate thereof would be equal to if the frequency of the low frequency clock signal equaled a target frequency for the low frequency clock, wherein the corresponding target value need not be an integer. The method also includes calibrating the low frequency clock by adjusting the frequency of the low frequency clock signal based on results of the comparing.

In certain such embodiments, the high frequency clock comprises a crystal oscillator, and the low frequency clock comprises a non-crystal oscillator. In specific embodiments, the high frequency clock is part of and/or for use by a radio frequency (RF) communication subsystem of the IMD and is selectively enabled and disabled to thereby reduce an amount of power consumed by the high frequency clock compared to if the high frequency clock was continuously enabled. In such embodiments, the low frequency clock is part of and/or for use by at least one of a sensor subsystem or a therapy subsystem of the IMD and is continuously enabled, and the calibrating the low frequency clock is performed during a period of time that the high frequency clock is enabled.

In certain embodiments, the calibrating the low frequency clock, by adjusting the frequency of the low frequency clock signal based on results of the comparing, comprises: increasing the frequency of the low frequency clock signal, when the average or the surrogate thereof is greater than the corresponding target value thereof, which is indicative of the frequency of the low frequency clock signal being less than the target frequency for the low frequency clock signal; and decreasing the frequency of the low frequency clock signal, when the average or the surrogate thereof is less than the corresponding target value thereof, which is indicative the frequency of the low frequency clock signal being greater than the target frequency for the low frequency clock signal.

In certain embodiments, the determining the average or the surrogate thereof (of how many high frequency clock cycles of the high frequency clock signal occur per low frequency clock cycle of the predetermined number N of the low frequency clock cycles of the low frequency clock signal) comprises: for each low frequency clock cycle or predetermined portion thereof, of the predetermined number N of low frequency clock cycles of the low frequency clock signal produced by the low frequency clock, producing a respective count value indicative of how many high frequency clock cycles occur during the low frequency clock cycle or predetermined portion thereof, to thereby produce N count values, wherein each of the N count values is an integer. An average of the N count values or a surrogate thereof is then determined.

In certain embodiments, each low frequency clock cycle or predetermined portion thereof corresponds to one of the following: a time from a rising edge of the low frequency clock signal to a following rising edge of the low frequency clock signal; a time from a falling edge of the low frequency clock signal to a following falling edge of the low frequency clock signal; a time from a rising edge of the low frequency clock signal to a following falling edge of the of the low frequency clock signal; or a time from a falling edge of the low frequency clock signal to a following rising edge of the low frequency clock signal.

In certain embodiments, each count value, of the N count values, comprises one of a lower possible count value or an upper possible count value. In such embodiments, the determining the average of the N count values or the surrogate thereof comprises determining the surrogate of the average of the N count values by: for each of the N count values, increasing a sum value by one when the count value is equal to the upper possible value, and not increasing the sum value when the count value is equal to the lower possible value, to thereby produce a total sum value; and dividing the total sum value by N to thereby produce the surrogate of the average of the N count values.

In certain embodiments, the determining the average or the surrogate thereof (of how many high frequency clock cycles of the high frequency clock signal occur per low frequency clock cycle of the predetermined number N of the low frequency clock cycles of the low frequency clock signal) comprises: storing the N count values in a first-in-first-out (FIFO) register of the IMD; using at least one processor of the IMD to determine, based on the N count values stored in the FIFO register, the average of the N count values or the surrogate thereof; and using the at least one processor to control the calibrating of the low frequency clock.

In certain embodiments, the determining the average or the surrogate thereof (of how many high frequency clock cycles of the high frequency clock signal occur per low frequency clock cycle of the predetermined number N of the low frequency clock cycles of the low frequency clock signal) comprises: determining an accumulated value that corresponds to how many high frequency clock cycles of the high frequency clock signal occur within the predetermined number N of low frequency clock cycles of the low frequency clock signal, wherein the accumulated value is an integer; and determining a quotient of the accumulated value divided by the predetermined number N. In certain such embodiments, the determining the accumulated value comprises: providing the low frequency clock signal produced by the low frequency clock to a first counter to thereby produce a first count value that is incremented each low frequency clock cycle of the low frequency clock signal; providing the high frequency clock signal produced by the high frequency clock to a second counter to thereby produce a second count value that is incremented each high frequency clock cycle of the high frequency clock signal; comparing the first count value to the predetermined number N to thereby determine when the first count value reaches the predetermined number N; and determining the accumulated value as being equal to the second count value when the first count value reaches the predetermined number N.

Certain embodiments of the present technology are related to an IMD comprising a low frequency clock, a high frequency clock, and a calibration subsystem. The low frequency clock is configured to produce a low frequency clock signal. The high frequency clock is configured to produce a high frequency clock signal having a frequency that is at least an order of magnitude greater than a frequency of the low frequency clock signal, wherein the high frequency clock when enabled consumes more power than the low frequency clock. The calibration subsystem is configured to determine an average, or a surrogate thereof, of how many high frequency clock cycles of the high frequency clock signal occur per low frequency clock cycle of a predetermined number N of low frequency clock cycles of the low frequency clock signal, wherein the predetermined number N is an integer that is at least 2. The calibration subsystem is also configured to compare the average or a surrogate thereof to a corresponding target value that the average or the surrogate thereof would be equal to if the frequency of the low frequency clock signal equaled a target frequency for the low frequency clock, wherein the corresponding target value need not be an integer; and calibrate the low frequency clock by adjusting the frequency of the low frequency clock signal based on results of the comparison. In certain such embodiments, the high frequency clock comprises a crystal oscillator, and the low frequency clock comprises a non-crystal oscillator. Further, the high frequency clock can be part of and/or for use by a RF communication subsystem of the IMD and is selectively enabled and disabled to thereby reduce an amount of power consumed by the high frequency clock compared to if the high frequency clock was continuously enabled. The low frequency clock can be part of and/or for use by at least one of a sensor subsystem or a therapy subsystem of the IMD and is continuously enabled. The calibration subsystem is configured to calibrate the low frequency clock during a period of time that the high frequency clock is enabled.

In certain embodiments, the calibration subsystem is configured to determine the average, or the surrogate thereof (of how many high frequency clock cycles of the high frequency clock signal occur per low frequency clock cycle of the predetermined number N of the low frequency clock cycles of the low frequency clock signal) by: producing a respective count value indicative of how many high frequency clock cycles occur during the low frequency clock cycle or predetermined portion thereof, for each low frequency clock cycle or predetermined portion thereof, of the predetermined number N of low frequency clock cycles of the low frequency clock signal produced by the low frequency clock, to thereby produce N count values; and determining an average of the N count values or a surrogate thereof. In certain such embodiments, each count value, of the N count values, comprises one of a lower possible count value or an upper possible count value; and the calibration subsystem is configured to determine the surrogate of the average of the N count values by: for each of the N count values, increasing a sum value by one when the count value is equal to the upper possible value, and not increasing the sum value when the count value is equal to the lower possible value, to thereby produce a total sum value; and dividing the total sum value by N to thereby produce the surrogate of the average of the N count values.

In certain embodiments, the calibration subsystem is configured to: increase the frequency of the low frequency clock signal, when the average or the surrogate thereof is greater than the corresponding target value thereof, which is indicative the frequency of the low frequency clock signal being less than the target frequency for the low frequency clock signal; and decrease the frequency of the low frequency clock signal, when the average or the surrogate thereof is less than the corresponding target value thereof, which is indicative the frequency of the low frequency clock signal being greater than the target frequency for the low frequency clock signal.

In certain embodiments, the calibration subsystem comprises a FIFO register configured to store the N count values. Additionally, the calibration subsystem comprises at least one processor configured to determine, based on the N count values stored in the FIFO register, the average of the N count values or the surrogate thereof; and control the calibrating of the low frequency clock based on the average of the N count values or the surrogate thereof.

In accordance with certain embodiments, the calibration subsystem is configured to determine the average or the surrogate thereof (of how many high frequency clock cycles of the high frequency clock signal occur per low frequency clock cycle of the predetermined number N of the low frequency clock cycles of the low frequency clock signal) by: determining an accumulated value that corresponds to how many high frequency clock cycles of the high frequency clock signal occur within the predetermined number N of low frequency clock cycles of the low frequency clock signal, wherein the accumulated value is an integer; and determining a quotient of the accumulated value divided by the predetermined number N.

In accordance with certain embodiments, the calibration subsystem comprises first and second counters. The first counter, which receives the low frequency clock signal produced by the low frequency clock, is configured to produce a first count value that is incremented each low frequency clock cycle of the low frequency clock signal. The second counter, which receives the high frequency clock signal produced by the high frequency clock, is configured to produce a second count value that is incremented each high frequency clock cycle of the high frequency clock signal. The calibration subsystem also includes a comparator configured to compare the first count value to the predetermined number N to thereby determine when the first count value reaches the predetermined number N. In such an embodiment, the accumulated value, which is divided by the predetermined number N to determine the average, is equal to the second count value when the first count value reaches the predetermined number N.

In accordance with a specific embodiments, an IMD includes a sensor or therapy subsystem including a low frequency clock, the low frequency clock implemented using a non-crystal oscillator, continuously enabled, and producing a low frequency clock signal. The IMD also includes a RF communication subsystem including a high frequency clock, the high frequency clock implemented using a crystal oscillator, selectively enabled and disabled, and when enabled consuming more power than the low frequency clock and producing a high frequency clock signal having a frequency that is at least an order of magnitude greater than a frequency of the low frequency clock signal. The IMD also includes a first counter that receives the low frequency clock signal produced by the low frequency clock, the first counter configured to produce a first count value that is incremented each low frequency clock cycle of the low frequency clock signal. Additionally, the IMD includes a second counter that receives the high frequency clock signal produced by the high frequency clock, the second counter configured to produce a second count value that is incremented each high frequency clock cycle of the high frequency clock signal. The IMD also includes first and second comparators, an averager, and a frequency adjuster. The first comparator is configured to compare the first count value to a predetermined number N to thereby determine when the first count value reaches the predetermined number N, wherein N is an integer that is at least 2. The averager is configured to determine an average of how many high frequency clock cycles of the high frequency clock signal occur per low frequency clock cycle of the predetermined number N of low frequency clock cycles of the low frequency clock signal. The second comparator is configured to compare the average (determined by the averager) to a target count value. The frequency adjuster is configured to adjust the frequency of the low frequency clock signal based on an output of the second comparator. In certain embodiments, one or more of the first comparator, the second comparator, the averager, and the frequency adjuster is/are implemented using a processor of the IMD.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

FIG. 3 is a high level flow diagram that is used to describe methods for calibrating a low frequency (LF) clock signal produced by a LF clock of an IMD, using a high frequency (HF) clock signal produced by a HF clock of the IMD, according to certain embodiments of the present technology.

DETAILED DESCRIPTION

Figure 1:
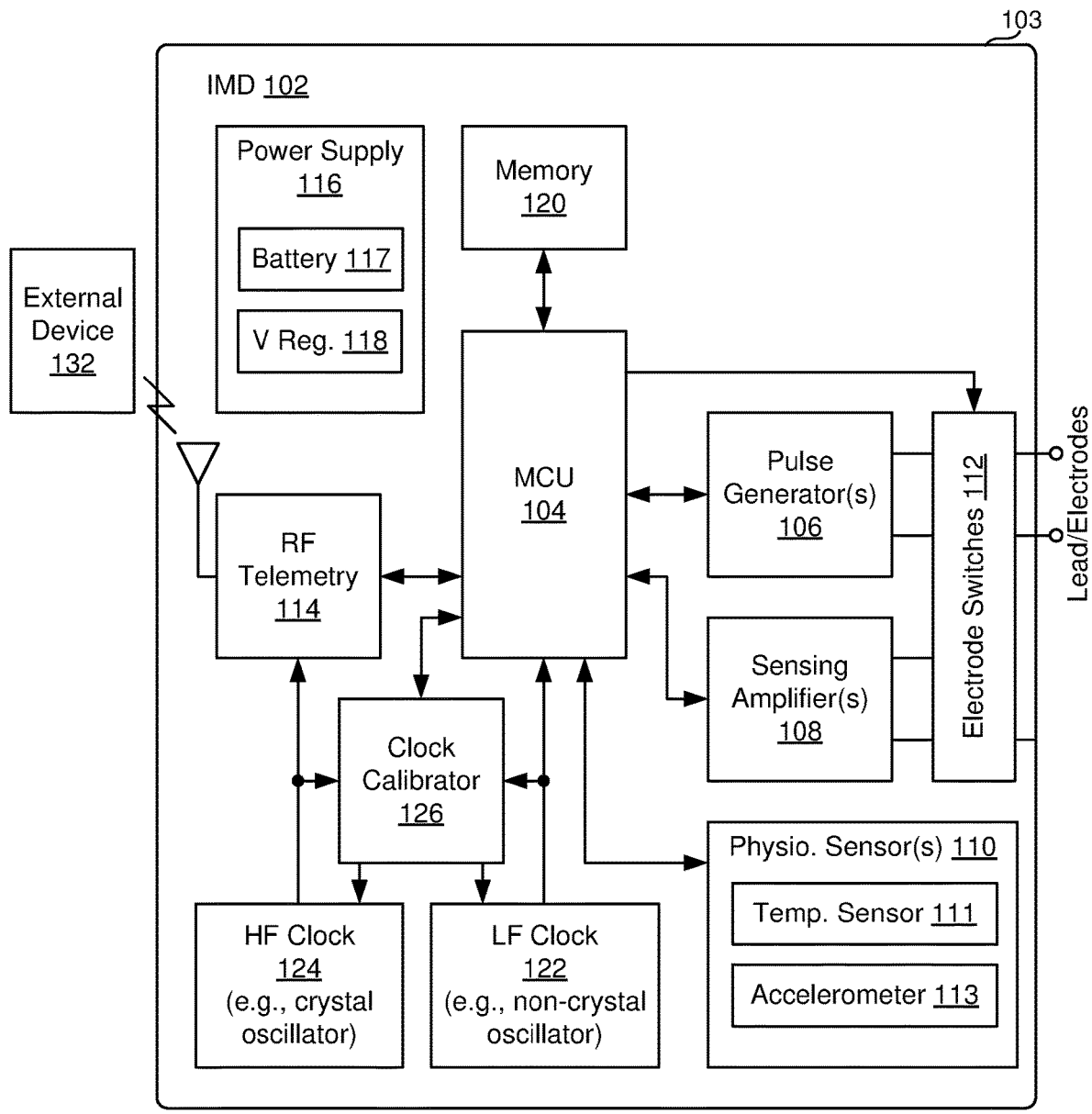
FIG. 1 is an electrical system block diagram of an example IMD.

As noted above, many IMDs have two timing sources, including an RF timing source that is used for RF communications, and a system timing source that is used to control the timing of therapy and/or sensing. As also noted above, in order to conserve energy, the RF timing source (that is used for RF communications) may be disabled or otherwise put into a low power mode when it is not being used. By contrast, the system timing source (that is used to provide therapy and/or sensing at appropriate times) is typically continuously enabled.

One way to provide the two timing sources in an IMD that uses RF communication, is to include two crystals within the IMD, including a high frequency crystal used for RF communication, and a lower frequency crystal used for controlling the timing of therapy and/or sensing. However, such an approach is not always practical, because as noted above crystals (especially relatively low frequency crystals) are relatively large, and thus, the inclusion of two large crystals in an IMD may adversely affect the overall size and package dimensions of the IMD. A reason that a single high frequency crystal is not typically used for both RF communication and controlling the timing of therapy and/or sensing is that it would be too costly, in terms of power consumption, to keep such a high frequency crystal continuously enabled such that it can always be available to control the timing of therapy and/or sensing.

For compliance reasons, the crystal oscillator used for RF communications cannot be replaced with a non-crystal oscillator. However, in accordance with certain embodiments of the present technology, in order to reduce the size of the oscillator used for providing therapy and/or sensing capabilities, a non-crystal oscillator is used instead of a crystal oscillator. Example types of non-crystal oscillators include resistor-capacitor (RC) oscillators, ring oscillators, voltage controlled oscillators (VCOs), and current controlled oscillators, just to name a few. A potential problem is that non-crystal oscillators is that they are not nearly as stable as crystal oscillators over time and temperature.

In accordance with certain embodiments of the present technology, a fast high frequency crystal oscillator (that is used for RF communication) is used to tune and calibrate a slower low frequency non-crystal oscillator (that is used to control the timing of therapy and/or sensing). With such embodiments, so long as the calibration is performed frequent enough, there is no discernable difference in frequency stability of the lower frequency non-crystal oscillator. More generally, in accordance with certain embodiments of the present technology, a high frequency (HF) clock that produces an HF clock signal is used to selectively calibrate a low frequency (LF) clock that produces a LF clock signal, wherein the terms HF and LF are relative to one another, and more specifically, the HF clock signal has a frequency that is at least an order of magnitude greater than a frequency of the LF clock signal. Before providing additional details of such embodiments, it is first useful to describe an example IMD with which such embodiments can be used or implemented.

FIG. 1 is a high level electrical system block diagram of an example IMD 102, which can be an LCP, traditional pacemaker, ICD, neurostimulator, or the like. Such an ICD can be, e.g., subcutaneous ICD (SubQ ICD), but is not limited thereto. The IMD 102 is shown as including a microcontroller unit (MCU) 104, pulse generator(s) 106, sensing amplifier(s) 108, physiologic sensor(s) 110, electrode switches 112, an RF telemetry module 114, a power supply 116, and memory 120. The IMD 102 is also shown as including a low frequency (LF) clock 122, a high frequency (HF) clock 124, and a clock calibrator 126.

The MCU 104 can control various modes of stimulation therapy. As is well known in the art, the MCU 104 (also referred to herein as a control unit or controller) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the MCU 104 includes the ability to process or monitor input signals (data) as controlled by a program code stored in a designated block of memory. The details of the design and operation of the MCU 104 are not critical to the technology. Rather, any suitable MCU 104 may be used that carries out the functions described herein. The use of microprocessor-based control circuits for performing timing and data analysis functions are well known in the art.

Where the IMD 102 is a cardiac stimulation device, the pulse generator(s) 106 can include an atrial pulse generator and/or a ventricular pulse generator that generate pacing stimulation pulses for delivery to cardiac tissue via electrodes. Such electrodes can be included on leads, or can be on or adjacent a housing 103 of the IMD 102, e.g., if the IMD 102 is an LCP. Where more than two electrodes are available for delivering stimulation pulses, the electrode switches 112 can be used to select specific combinations of electrodes under the control of the MCU 104. It is understood that in order to provide stimulation therapy in one or more of the four chambers of the heart, atrial and/or ventricular pulse generators (e.g., 106) may include dedicated, independent pulse generators, multiplexed pulse generators or shared pulse generators. The pulse generator(s) 106 are controlled by the MCU 104 via appropriate control signals to trigger or inhibit the stimulation pulses. Where the IMD 102 is a neurostimulator, the pulse generator(s) 106 can produce stimulation pulses that are for use in performing spinal cord stimulation (SCL), dorsal root ganglion (DRG) stimulation, deep brain stimulation (DBS), and/or the like. In the below description, unless stated otherwise, it will be assumed that the IMD 102 is a cardiac stimulation device.

Where the IMD 102 is a cardiac stimulation device, the MCU 104 can include a timing control module to control the timing of the stimulation pulses, including, but not limited to, pacing rate, atrioventricular (AV) delay, interatrial conduction (AA) delay, interventricular conduction (VV) delay and/or intraventricular delay (e.g., LV1-LV2 delay). The timing control module can also keep track of the timing of refractory periods, blanking intervals, noise detection windows, evoked response detection windows, alert intervals, marker channel timing, etc., which is well known in the art. The MCU 104 can also include an arrhythmia detector that can be used for determining desirable times to administer various therapies. The MCU 104 can also include a capture detection module and/or a morphology detection module. Depending upon the implementation, the various components of the MCU 104 may be implemented as separate software modules or the modules may be combined to permit a single module to perform multiple functions. In addition, although described as being components of the MCU 104, some or all of the above discussed modules may be implemented separately from the MCU 104, e.g., using one or more application specific integrated circuits (ASICs) or the like.

The electrode switches 112, which can also be referred to as switching circuitry 112, includes a plurality of switches for connecting the desired electrodes to the appropriate I/O circuits, thereby providing complete electrode programmability. Accordingly, the switching circuitry 112, in response to a control signal from the MCU 104, determines the polarity of the stimulation pulses (e.g., unipolar, bipolar, combipolar, etc.) by selectively closing the appropriate combination of switches (not shown) as is known in the art. The switching circuitry 112 can also switch among the various different combinations of electrodes.

The sensing amplifier(s) 108 can include, e.g., atrial and/or ventricular sensing amplifiers that are selectively coupled to various combinations of electrodes to provide for various different sensing vectors that can be used, e.g., for detecting the presence of cardiac activity in one or more of the four chambers of the heart. Accordingly, the sensing amplifier(s) 108 can include dedicated sense amplifiers, multiplexed amplifiers or shared amplifiers. The switching circuitry 112 determines the "sensing polarity" of the cardiac signal by selectively closing the appropriate switches, as is also known in the art. In this way, a clinician may program the sensing polarity independent of the stimulation polarity. Each sensing amplifier 108 can employ one or more low power, precision amplifiers with programmable gain and/or automatic gain control, bandpass filtering, and a threshold detection circuit, as known in the art, to selectively sense the cardiac signal of interest. The automatic gain control enables the IMD 102 to deal effectively with the difficult problem of sensing the low amplitude signal characteristics of atrial or ventricular fibrillation. The outputs of the sensing amplifier(s) 108 are connected to the MCU 104 which, in turn, is able to trigger or inhibit the one or more pulse generator(s) 106 in a demand fashion in response to the absence or presence of cardiac activity in the appropriate chambers of the heart.

For arrhythmia detection, the MCU 104 utilizes the sensing amplifier(s) 108 to sense cardiac signals to determine whether a rhythm is physiologic or pathologic. As used in this section "sensing" is reserved for the noting of an electrical signal, and "detection" is the processing of these sensed signals and noting the presence of an arrhythmia, an evoked response, an intrinsic event, or some other event being monitored for. The timing intervals between sensed events (e.g., AS, VS, and depolarization signals associated with fibrillation which are sometimes referred to as "F-waves" or "Fib-waves") can be classified by the MCU 104 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks). The arrhythmia detector, mentioned above, can be used to detect and characterize such arrhythmias.

Although not specifically shown in FIG. 1, cardiac signals can also applied to the inputs of an analog-to-digital (ND) data acquisition system that is configured to acquire intra-cardiac electrogram signals, convert the raw analog data into a digital signal, and store the digital signals for later processing and/or telemetric transmission to an external programmer or a bedside monitor or personal advisory module (PAM). The data acquisition system can be coupled to various leads and/or electrodes through the switching circuitry 112 to sample cardiac signals across any pair of desired electrodes. The MCU 104 is further coupled to memory 120 by a suitable data/address bus, or the like, wherein the programmable operating parameters used by the MCU 104 are stored and modified, as required, in order to customize the operation of IMD 102 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each pacing and shocking pulse to be delivered to the patient's heart within each respective tier of therapy. Other pacing parameters include base rate, rest rate and circadian base rate.

Advantageously, the operating parameters of the IMD 102 may be non-invasively programmed into the memory 120 through an RF telemetry circuit 114 in telemetric communication with an external device or bedside monitor 132, such as a programmer, transtelephonic transceiver or a diagnostic system analyzer. The RF telemetry circuit 114, which can also be referred to as an RF communication subsystem, is activated by the MCU 104 by a control signal. The RF telemetry circuit 114 advantageously allows intra-cardiac electrograms and status information relating to the operation of the IMD 102 (as contained in the MCU 104 or memory 120) to be sent to the external device 132 through an established communication link. An internal warning device, not specifically shown, may be provided for generating perceptible warning signals to the patient via vibration, voltage or other methods.

The physiologic sensors 110 can include a temperature sensor 111, an accelerometer 113, and/or other types of physiologic sensors, commonly referred to as a "rate-responsive" sensor because they can be used to adjust pacing stimulation rate according to the exercise state of the patient. However, the physiological sensor(s) 110 may further be used to detect changes in cardiac output, changes in the physiological condition of the heart, or diurnal changes in activity (e.g., detecting sleep and wake states) and to detect arousal from sleep. Accordingly, the MCU 104 can respond by adjusting the various pacing parameters (such as rate, AV delay, VV delay, etc.) at which the pulse generator(s) 106 generate stimulation pulses. While shown as being included within the IMD 102, it is to be understood that one or more of the physiologic sensor(s) 110 may also be external to the IMD 102, yet still be implanted within or carried by the patient. A common type of rate responsive sensor is an activity sensor incorporating an accelerometer or a piezoelectric crystal, which is mounted within the housing 103 of the IMD 102. Other types of physiologic sensors are also known, for example, sensors that sense the oxygen content of blood, respiration rate and/or minute ventilation, pH of blood, ventricular gradient, stroke volume, cardiac output, contractility, etc.

The power supply 116, which can include a battery 117 and a voltage regulator 118, provides operating power to all of the circuits or subsystem shown in FIG. 1. The specific type of battery 117 included in the IMD 102 can vary depending on the capabilities of IMD 102. If the IMD 102 only provides low voltage therapy, a lithium iodine or lithium copper fluoride cell typically may be utilized as the battery 117. If the IMD 102 provides shocking therapy, the battery 117 should be capable of operating at low current drains for long periods, and then be capable of providing high-current pulses (for capacitor charging) when the patient requires a shock pulse. The battery 117 should also have a predictable discharge characteristic so that elective replacement time can be detected. Accordingly, appropriate batteries are employed. One or more voltage regulators 118 can step up or step down a voltage provide by the battery 117 to produce one or more predetermined voltages useful for powering the various circuits or subsystems of the IMD 102.

The IMD 102 can include additional and/or alternative types of circuits or subsystems, not specifically shown in FIG. 1. For example, the IMD 102 can also include an impedance measurement circuit that can be used for providing lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. Such an impedance measurement circuit can be coupled to the switching circuitry 112 so that any desired combination of electrodes may be used.

In the case where the IMD 102 is intended to operate as an ICD system, it detects the occurrence of an arrhythmia, and automatically applies an appropriate electrical shock therapy to the heart aimed at terminating the detected arrhythmia. To this end, the MCU 104 can further control a shocking circuit (not shown) to generates shocking pulses of low (up to 0.1 joules), moderate (0.1-10 joules) or high energy (11 to 40 joules or more), as controlled by the MCU 104. Such shocking pulses are applied to the heart of the patient through at least two shocking electrodes, such as, a left atrial (LA) coil electrode, a right ventricular (RV) coil electrode, and/or a superior vena cava (SVC) coil electrode. The housing 103 may act as an active electrode in combination with another electrode, or as part of a split electrical vector using the SVC coil electrode or the LA coil electrode (i.e., using the RV electrode as a common electrode). Cardioversion shocks are generally considered to be of low to moderate energy level (so as to minimize pain felt by the patient), and/or synchronized with a R-wave and/or pertaining to the treatment of tachycardia. Defibrillation shocks are generally of moderate to high energy level (i.e., corresponding to thresholds in the range of 4-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses. A shocking circuit can include, e.g., a charge circuit and the charge capacitor(s) discussed above, but is not limited thereto.

The above described IMD 102 was described as an example cardiac stimulation device. One of ordinary skill in the art would understand that embodiments of the present technology can be used with alternative types of implantable devices. Accordingly, embodiments of the present technology should not be limited to use only with the above described device.

The RF telemetry circuit 114 can be the Bluetooth Low Energy (BLE) radio, or some other RF communication subsystem, that is implemented in an RF integrated circuit (IC). The remaining set of circuits or subsystems of the IMD 102 shown in FIG. 1, or just a subset thereof, can be implemented in a custom application specific IC (ASIC), which can also be referred to as a custom chip. In other words, the terms IC and chip are used interchangeably herein. Depending on the specific IMD, there may be additionally IC's. The custom IC can host the IMD's application and have all the associated circuits for sensing, pacing, high voltage (HV) therapy, etc. The RF chip, which is used to provide RF communication, can include a high-speed (aka high frequency) crystal oscillator. The connection between the RF chip and the custom chip is typically a standard serial interface, such as serial peripheral interface (SPI) and a few general-purpose input-outputs (GPIO), but can alternatively or additionally include a parallel interface.

As noted above, the IMD 102 is shown as including the LF clock 122, the HF clock 124, and the clock calibrator 126. In FIG. 1, the clock calibrator 126 is shown as being external to the MCU 104, but in specific embodiments can be completely or at least partially implementing by the MCU 104. In accordance with certain embodiments, the HF clock 124 includes a crystal oscillator, and the LF clock 122 is devoid of a crystal oscillator, and rather, includes a non-crystal oscillator. Example types of non-crystal oscillators which can be included in the LF clock 122 include, but are not limited to, an RC oscillator, an LC oscillator, a VCO, or a ring oscillator, just to name a few. The HF clock 124 produces a HF clock signal having a frequency that is at least an order of magnitude greater than a frequency of the LF clock signal produced by the LF clock 122. For example, if the LF clock signal is ~32 kHz, then the HF clock signal is at least 320 kHz, and likely, is in the MHz range. For more specific examples, the LF clock 122 can produce a LF clock signal having a frequency of 32.768 kHz, and the HF clock 124 can produce a HF clock signal having a frequency of 16 MHz, 32 MHz or 48 MHz, but is not limited thereto. Accordingly, in certain embodiments, the HF clock 124 produces a high frequency clock signal having a frequency that is at least two or three orders of magnitude greater than a frequency of the LF clock signal produced by the LF clock 122. In such embodiments, the HF clock 124 when enabled consumes more power than the LF clock 122.

In certain such embodiments, the HF clock 124 is part of and/or for use by the RF communication subsystem 114 of the IMD 102 and is selectively enabled and disabled by the MCU 104 to thereby reduce an amount of power consumed by the HF clock 124, compared to if the HF clock 124 was continuously enabled. For example, the MCU 104 may enable (turn on) the RF communication subsystem 114 to allow the IMD 102 to determine whether an external device 132 or another implanted device (not shown) is attempting to establish an RF communication session. The MCU 104 may also enable the RF communication subsystem 114 during RF communication sessions with an external device 132 or another implanted device (not shown), and/or the like. In accordance with certain embodiments, the LF clock 122 is continuously enabled and is part of and/or for use by a sensor subsystem and/or a therapy subsystem of the IMD 102 and is continuously enabled. For example, the LF clock signal (produced by the LF clock 122) can be used to control the timing of or associated with the pulse generator(s) 106, the sensing amplifier(s) 108, the electrode switches 112, the physiologic sensor(s) 110, and/or the like. The LF clock signal (produced by the LF clock 122) can also be provided to MCU 104 and used by the MCU 104 to provide timing control of other circuits or subsystems, as well as to providing timing control of its own functions. A sensor subsystem of the IMD 102 can include, e.g., the physiologic sensor(s) 110. A therapy subsystem of the IMD 102 can include, e.g., the pulse generator(s) and the sensing amplifier(s).

Figure 2A:
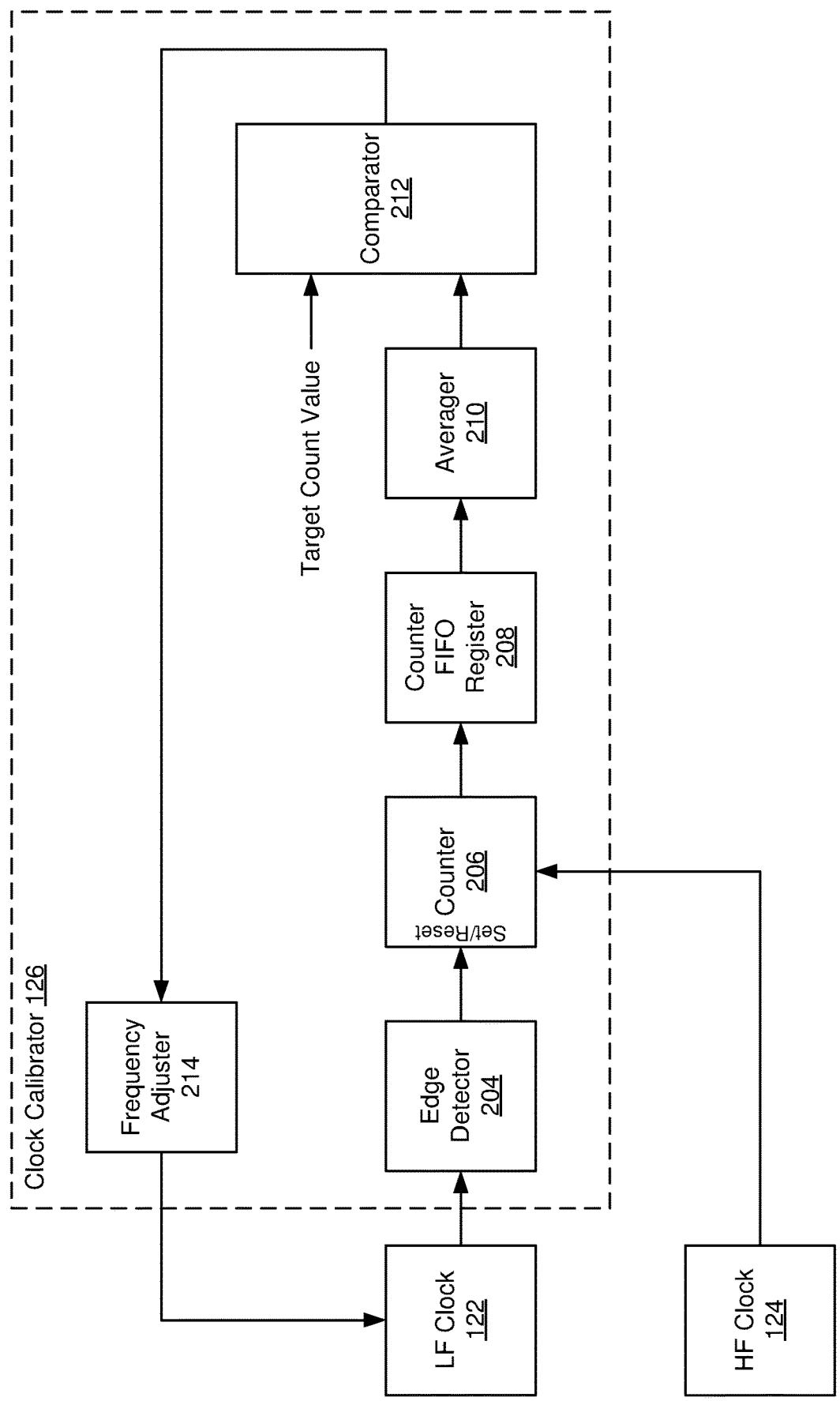
FIG. 2A shows additional example details of the clock calibrator of the IMD introduced in FIG. 1, according to an embodiment of the present technology.

The high level block diagram of FIG. 2A will now be used to provide additional details of the clock calibrator 126, according to an embodiment of the present technology. Referring to FIG. 2A, the clock calibrator 126 is shown as including an edge detector 204, a counter 206, a counter FIFO register 208, an averager 210, a comparator 212, and a frequency adjuster 214 that are connected in a feedback loop. The LF clock signal, that is output by the LF clock 122, is shown as being provided to the edge detector 204. The HF clock signal, that is output by the HF clock 124, is shown as being provided to the counter 206. In the embodiment shown in FIG. 2A, it is assumed that the HF clock 124 is crystal based and that the HF clock signal it produces is highly stable. It is also assumed that the LF clock 122 is not crystal based and that the LF clock signal it produces is less stable than the HF clock signal, and more specifically, will slowly drift over time, and will more quickly drift over changes in temperature.

The edge detector 204 includes an input and an output. In FIG. 2A, the LF clock signal that is produced by the LF clock 122 is provided to the input of the edge detector 204, and the output signal of the edge detector 204 is provided to a set/reset input of the counter 206. The edge detector 204 can be configured to detect rising edges of the signal provided to its input, and the output signal of the edge detector 204 can briefly go from LOW to HIGH whenever the edge detector 204 detects a rising edge of the signal provided to its input. In other words, the edge detector 204 can produce a short pulse whenever the edge detector 204 detects a rising edge. Alternatively, or additionally, the edge detector 204 can be configured to detect falling edges of the signal provided to its input. Unless stated otherwise, for the much of the following discussion it will be assumed that the edge detector 204 outputs a short pulse in response to detecting a rising edge of the LF clock signal provided to the input of the edge detector 204. In such an embodiment, the edge detector 204 can be used to identify each clock cycle of the LF clock. The edge detector 204 can be implemented, for example, using one or more flip-flops and/or logic gates, as is known in the art, but is not limited thereto.

The counter 206 includes a set/reset input, a signal input, and an output. The short pulses that are output by the edge detector 204 are provided to the set/reset input of the counter 206. The HF clock signal produced by the HF clock 124 is provided to the signal input of the counter 206. In such a configuration, the counter 206 is configured to selectively produce a count value indicative of how many high frequency clock cycles occur during a low frequency clock cycle. More specifically, the counter 206, in response to receiving a short pulse from the edge detector 204, begins counting the number of pulses in the HF clock signal provided to the signal input of the counter 206. This can be achieved, for example, by the counter 206 incrementing a count value in response to each rising edge of the HF clock signal. Thereafter, in response to receiving the next short pulse from the edge detector 204, the counter 206 transfers its count value to the counter FIFO register 208, is reset, and begins counting up again.

The counter FIFO register 208 can be implemented as a first-in-first-out (FIFO) register that is configured to store N count values, where N is an integer that is at least 2, and is likely significantly larger than 2. For example, N is likely at least 10, but may be higher or lower, depending upon the resolution desired. The averager 210 is configured to produce an average count value, of the N count values stored in the counter FIFO register 208. While each of the N count values is an integer, the average count value need not be an integer, and is likely not an integer. The averager 210 can be implemented as a dedicated circuit, or can be implemented by the MCU 104, but is not limited thereto.

In accordance with certain embodiments, a function of the clock calibrator 126 is to cause the average count value that is output by the averager 210 to be equal to (or within some acceptable tolerance of) a target count value that the average of the N count values would be equal to if the frequency of the LF clock signal equaled (i.e., was the same as) a target frequency for the LF clock signal. Such a target count value need not be an integer, and is likely not an integer. For an example, assume that the target frequency for the LF signal produced by the LF clock 122 (which includes a non-crystal oscillator) is 32.768 kHz, and that the frequency of the HF signal produced by the HF clock 124 (which includes a crystal-oscillator) is 16 MHz. Continuing with this example, the target count value can be calculated using the following equation:

$$\text{target count value} = \frac{f_{HF}}{f_{LF\ target}}$$

where, $f_{HF}$ is the frequency of the HF clock signal produced by the HF clock 124, $f_{LF\ target}$ is the target frequency of the LF clock signal produced by the LF clock 122, and target count value is what the average of the N count values would be equal to if the frequency of the LF clock signal was equal to the target frequency for the LF clock 122.

Continuing with the above example, the target count value would be 488.281, since 16 MHz/32.768 kHz=488.281. As can be appreciated from this example, the target count value need not be an integer, and the HF clock signal need not be an integer multiple of the LF clock signal.

Still referring to FIG. 2A, the comparator 212 is configured to compare the average of the N count values (stored in the counter FIFO register 208), as determined by the averager 210, to the target count value. The target count value can be stored in a dedicated register, and/or can be provided by the MCU 104, but is not limited thereto. The comparator 212 can be implemented in various different manners, depending upon the implementation. In one embodiment, the comparator 212 outputs a first binary logic level (e.g., HIGH) whenever the average of the N count values is more than the target count value, and outputs a second binary logic level (e.g., LOW) whenever the average of the N count values is less than or equal to the target count value. Alternatively, the comparator 212 outputs the second binary logic level (e.g., LOW) whenever the average of the N count values is more than the target count value, and outputs the first binary logic level (e.g., HIGH) whenever the average of the N count values is less than or equal to the target count value. In still another embodiment, the comparator 212 can subtract the target count value from the average of the N count values (or vice versa), in order to thereby determine a magnitude of the difference between the these two values, and if the difference is a signed value, then the difference also provides an indication of which of the two values is greater.

The output of the comparator 212 is shown as being provided to the frequency adjuster 214, which adjusts the frequency of the LF clock signal, by either increasing or decreasing the frequency of the LF clock signal such that it moves toward the target frequency for the LF clock signal.

When the average of the N count values is greater than the target value thereof (e.g., 488.281), that is indicative the frequency of the LF clock signal being less than the target frequency for the LF clock signal. Conversely, when the average of the N count values is less than the target value thereof (e.g., 488.281), that is indicative the frequency of the LF clock signal being greater than the target frequency for the LF clock signal. Accordingly, the frequency adjuster 214 can be configured to increase the frequency of the LF clock signal, when the average of the N count values (or a surrogate thereof) is greater than the corresponding target value thereof, which is indicative the frequency of the LF clock signal being less than the target frequency for the LF clock signal. Additionally, the frequency adjuster 214 can be configured to decrease the frequency of the LF clock signal when the average of the N count values (or a surrogate thereof) is less than the corresponding target value thereof, which is indicative the frequency of the LF clock signal being greater than the target frequency for the LF clock signal.

The frequency adjuster 214, and more generally the clock calibrator 126, can adjust the frequency of the LF clock in various different manners, which may depend upon how the non-crystal oscillator of the LF clock 122 is implemented. For example, where the non-crystal oscillator of the LF clock 122 is an RC oscillator, the frequency of the LF clock can be adjusted by adjusting resistor and/or capacitor values, or changing which resistor(s) and/or capacitor(s) are selected from banks thereof. Where the non-crystal oscillator of the LF clock 122 is an LC oscillator, the frequency of the LF clock can be adjusted by adjusting inductor and/or capacitor values, or changing which inductor(s) and/or capacitor(s) is/are selected from banks thereof. For still another example, where the non-crystal oscillator of the LF clock 122 is implemented as a VCO, the frequency adjuster 214, and more generally the clock calibrator 126, can adjust the frequency of the LF clock by increasing or decreasing a voltage provided to a voltage input of the VCO. While the frequency adjuster 214 is shown as being separate from the LF clock 122, it would be possible to implement the frequency adjuster 214 as part of the LF clock 122, depending upon the specific implementation. For another example, it would also be possible for the frequency adjuster 214 to be implemented by the MCU 104. Additional components of the clock calibrator 126, such as the averager 210 and/or the comparator 212, but not limited thereto, may also be implemented by the MCU 104.

The embodiments summarized with reference to FIG. 2A provide a phase detector (also known as a phase-frequency detector), which can be used to detect fractional differences in phase, essentially providing a form of a phase locked loop (PLL). More specifically, the edge detector 204, counter 206, counter FIFO register 208, averager 210, and comparator 212 collectively provide the functions of a phase detector and a low pass filter (LPF) of a PLL, but in a different manner than in a more conventional PLL. In such embodiments, the output of the comparator 212 is indicative of a phase and frequency difference between the LF clock signal produced by the LF clock 122 and the target frequency for the LF clock signal.

The frequency stability of a crystal oscillator, such as the one included in the HF clock 124, is often given in parts per million (PPM), which provides an indication of a crystal oscillator's frequency deviation from its ideal frequency. The deviation from ideal (Δf) can be expressed as follows:

$$\Delta f = \frac{f * PPM}{10^6}$$

where,
Δf is the deviation from ideal (in Hz),
f is the center frequency of the clock signal produced by the crystal oscillator (in Hz), and
PPM is the frequency variation in parts per million.

For an example, if a crystal oscillator has an output frequency of 1 MHz (1000000 Hz) and it has a frequency stability of 5 PPM, it will vary in frequency by 5 Hz. For most common crystals, a 100-500 PPM crystal is considered adequate for therapy and/or sensing applications provided by an IMD. This means for a 32.768 kHz, 100 PPM crystal, the actual frequency is between 32.7647 kHz and 32.7713 kHz. To adequately replace a crystal oscillator with an RC oscillator or some other non-crystal oscillator, for inclusion in the LF clock 122, the clock calibrator 126 needs to be able to distinguish differences of approximately +/−4 Hz.

In the embodiments of the present technology described above with reference to FIG. 2A, a phase-frequency detector is implemented by counting the number of HF clock signal periods in one period of the LF clock signal. This is accomplished using the counter 206 sampled at the HF clock signal to sample the LF clock signal, as shown in FIG. 2A. In certain such embodiments, upon each rising edge of the LF clock signal, the counter 206 is started. Upon the next rising edge of the LF clock signal the counter 206 is stopped, reset, then restarted. The count value is loaded into the counter FIFO register 208. The edge detector 204 detects rising edges of the incoming LF clock signal and is used to control the operation of the counter 206, i.e., to trigger or increment the counter. The counter FIFO register 208 can be read by the MCU 104 for further processing, e.g., to provide the functions performed by the averager 210, comparator 212, and/or the frequency adjuster 214. The counter FIFO register 208 can always contain the last N count values, where N is the size of the FIFO when full, and thereby the counter FIFO register 208 can store count values at each period of the LF clock signal.

Each count value in the counter FIFO register 208 represents the number of HF clock periods in one period the LF clock signal by the following relationship:

$$f_{LF} = \frac{f_{HF}}{CNT}$$

This count value (CNT) will change in time since the HF clock signal is likely not an integer multiple of the LF clock signal. A high degree of resolution is needed to be able to detect a small change in frequency. This change can be detected by averaging the count values. The frequency of the LF clock signal can then be estimated by:

$$f_{LF} = \frac{f_{HF}}{\text{avg}(CNT)}$$

For example, to detect +/−4 Hz from a 32.768 kHz LF clock signal, listed below in Table 1 are representative lower and upper limit count values where the HF clock signal has frequencies of 16 MHz, 32 MHz, and 48 MHz:

TABLE 1

| Reference Clock Freq. (MHz) | Period (ns) | Lower Limit Count | Upper Limit Count | Δ Count |
|---|---|---|---|---|
| 16 | 62.5 | 488.341 | 488.222 | 0.119 |
| 32 | 31.25 | 976.682 | 976.443 | 0.239 |
| 48 | 20.83 | 1465.023 | 1464.665 | 0.358 |

The amount of averaging required depends on several factors including the frequencies of the HF and LF clock signals. To illustrate the relationship, Table 2 below includes results of a simulation of the phase-frequency detector, which results show the frequency error based on the number (N) of count values averaged, where the HF clock signal has a center frequency of 48 MHz, and the LF clock signal is varied from 32.760 kHz to 32.780 kHz.

TABLE 2

| Number (N) of count values averaged | Root Mean Square Error (RMSE) in Hz |
|---|---|
| 8 | 2.09 |
| 32 | 1.25 |
| 128 | 1.17 |

Averaging large sets of data require summing large sets of numbers, thus complicating the arithmetic required by the MCU 104 and/or averager 210. In accordance with certain embodiments, a simplified approach is to note the number of differences in the counts. For most samples, the same count value is recorded for each period of the LF clock signal. Periodically a one count difference value is recorded. This is expected since the average value is between these two values. In a simplified embodiment the number of differences in the entire data set can be computed. The average value can be computed based on ratio of differences using the following formula:

$$AVG = CNT_{min} + \frac{N_{maj}}{N_{samples}}$$

where, $CNT_{min}$ is the minimum count value, $N_{maj}$ is the number of elements in the data set that contain the majority count, and $N_{samples}$ is the total number of elements (e.g., count values) in the data set.

A benefit of including the edge detector 204 within the clock calibrator 126 is that it can be used to detect both the rising edge to the falling edge, the rising edge to the next rising edge, or the falling edge to the next falling edge, of each clock pulse in order to perform duty cycle measurements and adjustments, since its generally desirable to have the clock duty cycle be as close to 50% as possible. However, it is also within the scope of the embodiments of the present technology to eliminate the edge detector 204, which results in the embodiment shown in FIG. 2B.

Figure 2B:
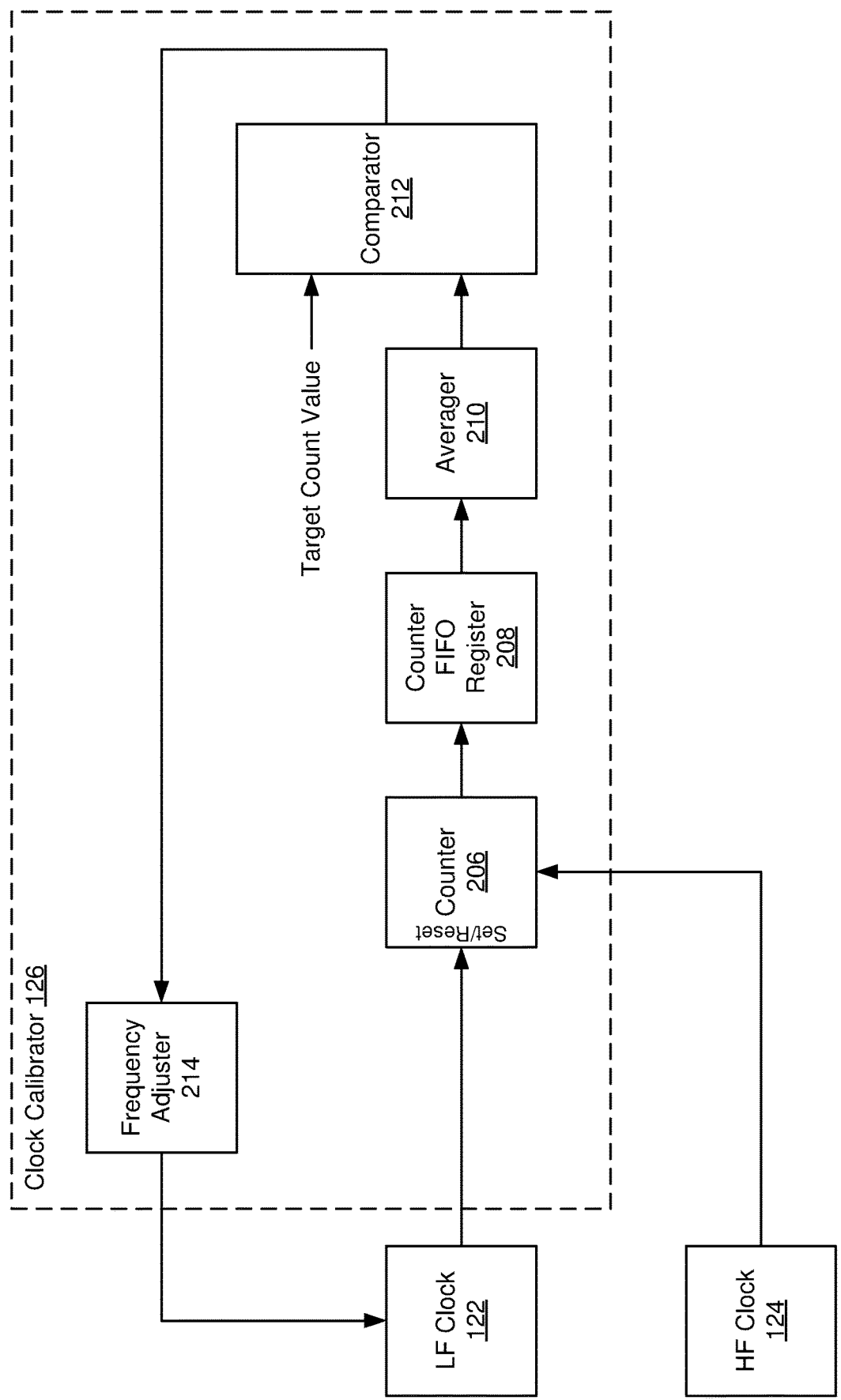
FIG. 2B shows example details of the clock calibrator of the IMD introduced in FIG. 1, according to another embodiment of the present technology.

In the embodiment of FIG. 2B, the LF clock signal (produced by the LF clock 122) is provided directly to the set/reset input of the counter 206. The counter 206, as was the case in the embodiment of FIG. 2A, is configured to selectively produce a count value indicative of how many HF clock cycles occur during a LF clock cycle. More specifically, the counter 206, in response to receiving a rising edge (or alternatively, a falling edge) of the LF clock signal, begins counting the number of pulses in the HF clock signal provided to the signal input of the counter 206. This can be achieved, for example, by the counter 206 incrementing a count value in response to each rising edge of the HF clock signal (or alternatively, in response to each falling edge of the HF clock signal). Thereafter, in response to receiving the next rising edge (or alternatively, the next falling edge) of the LF clock signal, the counter 206 transfers its count value to the counter FIFO register 208, is reset, and begins counting up again. In the embodiment of FIG. 2B, the counter 206, counter FIFO register 208, averager 210, and comparator 212 collectively provide the functions of a phase detector and a LPF of a PLL, but in a different manner than in a more conventional PLL.

Figure 2C:
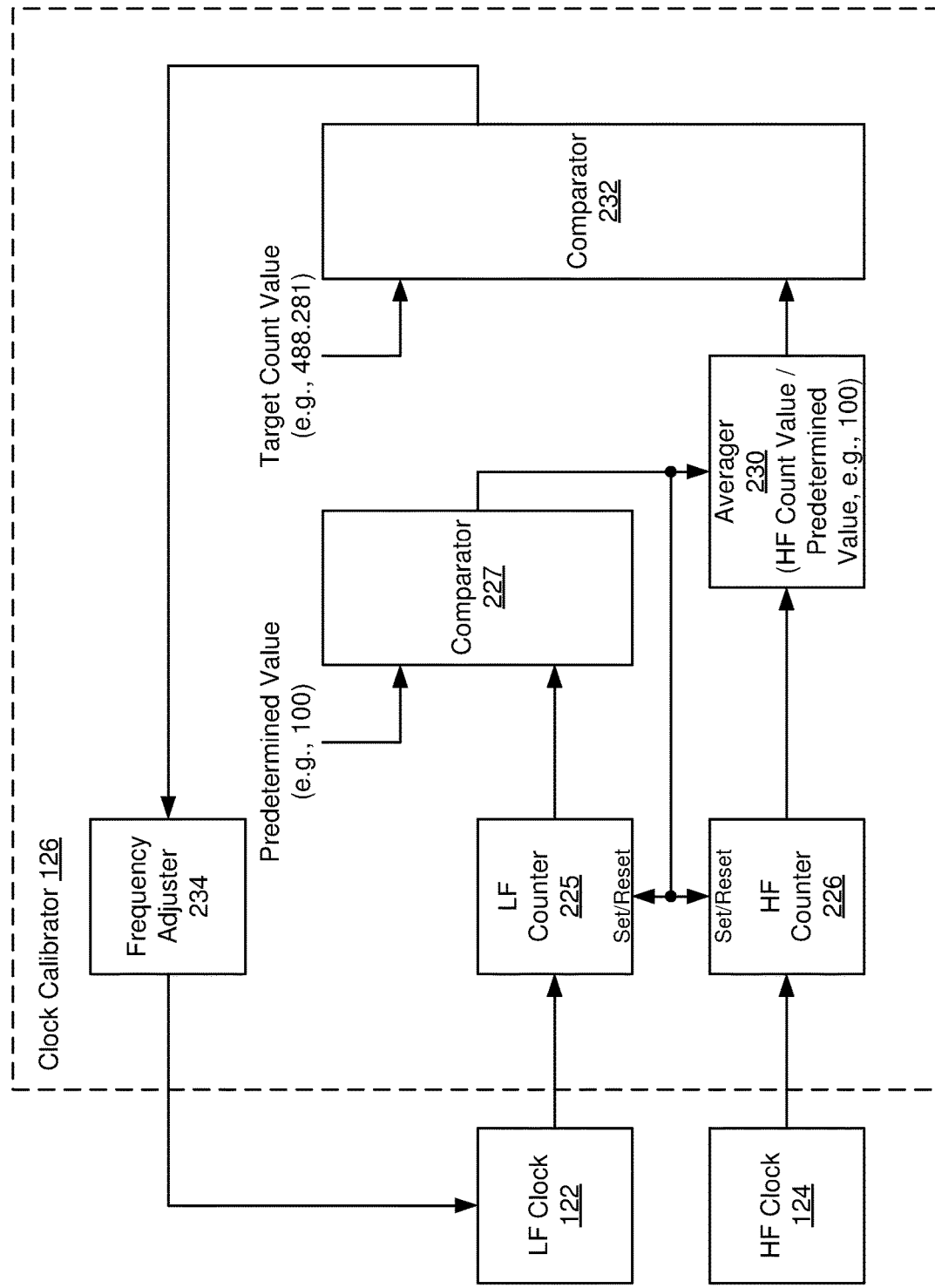
FIG. 2C shows example details of the clock calibrator of the IMD introduced in FIG. 1, according to a further embodiment of the present technology.

The high level block diagram of FIG. 2C will now be used to provide details of the clock calibrator 126, according to a further embodiment of the present technology. Referring to FIG. 2C, the clock calibrator 126 is shown as including a counter 225, a counter 226, a comparator 227, an averager 230, a comparator 232, and a frequency adjuster 234. For reasons that will be clear from the following description, the counter 225 can be more specifically referred to as a low frequency (LF) counter 225, and the counter 226 can be more specifically referred to as a high frequency (HF) counter 226. The LF clock signal, that is output by the LF clock 122, is shown as being provided to the LF counter 225. The HF clock signal, that is output by the HF clock 124, is shown as being provided to the HF counter 226. In the embodiment shown in FIG. 2C, it is assumed that the HF clock 124 is crystal based and that the HF clock signal it produces is highly stable. It is also assumed that the LF clock 122 is not crystal based and that the LF clock signal it produces is less stable than the HF clock signal, and more specifically, will slowly drift over time, and will more quickly drift over changes in temperature.

The LF counter 225 and the HF counter 226 each includes a set/reset input, a signal input, and an output. The LF clock signal (produced by the LF clock 122) is provided to the signal input of the LF counter 225. Similarly, the HF clock signal (produced by the HF clock 124) is provided to the signal input of the HF counter 226. In such a configuration, the LF counter 225 is incremented in response to each rising edge (or alternatively, each falling edge) of the LF clock signal. The LF count value, produced by the LF counter 225, is provided to the comparator 227. The comparator 227 compares the LF count value to a predetermined value, e.g., 100. When the LF count value reaches (is equal to or exceeds) the predetermined value (e.g., 100), the output of the comparator 227 transitions from a LOW to HIGH logic state (or vice versa). This output of the comparator 227 is provided to the set/reset inputs of the LF counter 225 and the HF counter 226, as well as to the averager 230.

The HF counter 226 is incremented in response to each rising edge (or alternatively, each falling edge) of the HF clock signal produced by the HF clock 124. The HF count value, produced by the HF counter 226, is provided to the averager 230. In such an embodiment, the HF counter 226 continues to be incremented until the output of the comparator 227 transitions from a LOW to HIGH logic state (or vice versa), and thus, until the LF count value is equal to the predetermined value (e.g., 100). This predetermined value can also be referred to as a predetermined number N, where N is an integer that is at least 2, and is preferably at least 10, and can be higher, e.g., 100 or greater, but is not limited thereto. Accordingly, the HF counter 226 produces a HF count value indicative of how many HF clock cycles occurred during the predetermine number N (e.g., 100) of LF clock cycles. At that point, the averager 230 determines the average number of HF clock cycles per LF clock cycle by determining the quotient of the HF count value divided by the predetermine value N (e.g., 100). The comparator 232 compares the average value (that is output by the averager 230) to the target count value (e.g., 488.281), and the output of the comparator 232 is provided to the frequency adjuster 234.

The output of the comparator 232 is shown as being provided to the frequency adjuster 234, which adjusts the frequency of the LF clock signal, by either increasing or decreasing the frequency of the LF clock signal such that it moves toward the target frequency for the LF clock signal. When the average value (produced by the averager 230) is greater than the target value thereof (e.g., 488.281), that is indicative the frequency of the LF clock signal being less than the target frequency for the LF clock signal. Conversely, when the average value (produced by the averager 230) is less than the target value thereof (e.g., 488.281), that is indicative the frequency of the LF clock signal being greater than the target frequency for the LF clock signal. Accordingly, the frequency adjuster 234 can be configured to increase the frequency of the LF clock signal, when the average value (or a surrogate thereof) is greater than the corresponding target value thereof, which is indicative the frequency of the LF clock signal being less than the target frequency for the LF clock signal. Additionally, the frequency adjuster 234 can be configured to decrease the frequency of the LF clock signal when the average value (or a surrogate thereof) is less than the corresponding target value thereof, which is indicative the frequency of the LF clock signal being greater than the target frequency for the LF clock signal. The frequency adjuster 234, and more generally the clock calibrator 126, can adjust the frequency of the LF clock in various different manners, examples of which were already provided above in the discussion of FIG. 2C, and thus, need not be repeated. In still another embodiment, an edge detector (the same or similar to the edge detector 204 in FIG. 2A) can be included between the LF clock 122 and the LF counter 225, if there is a desired to track and adjust the duty cycle of the LF clock signal, e.g., to keep it as close to 50% as possible, if so desired.

In accordance with certain embodiments, a software algorithm determines each of these variables and performs one calculation to determine the actual frequency of the LF clock signal. The frequency of the LF clock signal can then be adjusted to get closer to the desired frequency. Various implementations of this entire algorithm are discussed below with reference to FIGS. 3-5. Such a calibration can be performed either periodically as the LF clock 122 can drift in time, or an operation condition changes such as temperature.

The HF clock 124 is based on a crystal with low drift (e.g., most BLE crystals are around 10 PPM). The power during calibration can be high to enable the HF clock 124 and direct its HF clock signal to the clock calibrator 126. In accordance with certain embodiments, the calibration procedure is quick, on the order of only a few microsecond (μs), and this procedure only needs to happen periodically, e.g., on a weekly or monthly basis. Since this is so infrequent, the power/longevity impact on an IMD is negligible.

Advantageously, embodiments of the present technology provide for a lower part count and lower cost solution than a traditional approach of using two crystals. By using a non-crystal oscillator to provide the system clock, an IMD can be made smaller and/or the volume of the IMD that is physically occupied by the system clock can be made smaller (since traditional 32 kHz crystal oscillators are fairly large). Crystals are some of the most expensive components of an IMD. Thus, the cost of an IMD can be significantly reduced by including only one crystal oscillator in the IMD, rather than two crystal oscillators. Embodiments of the present technology allow for a trade-off of power and stability. The more stability required the more often calibration is performed. A greatly simplified frequency/phase calculation and procedure is provided that does not require complicated math.

Figure 4:
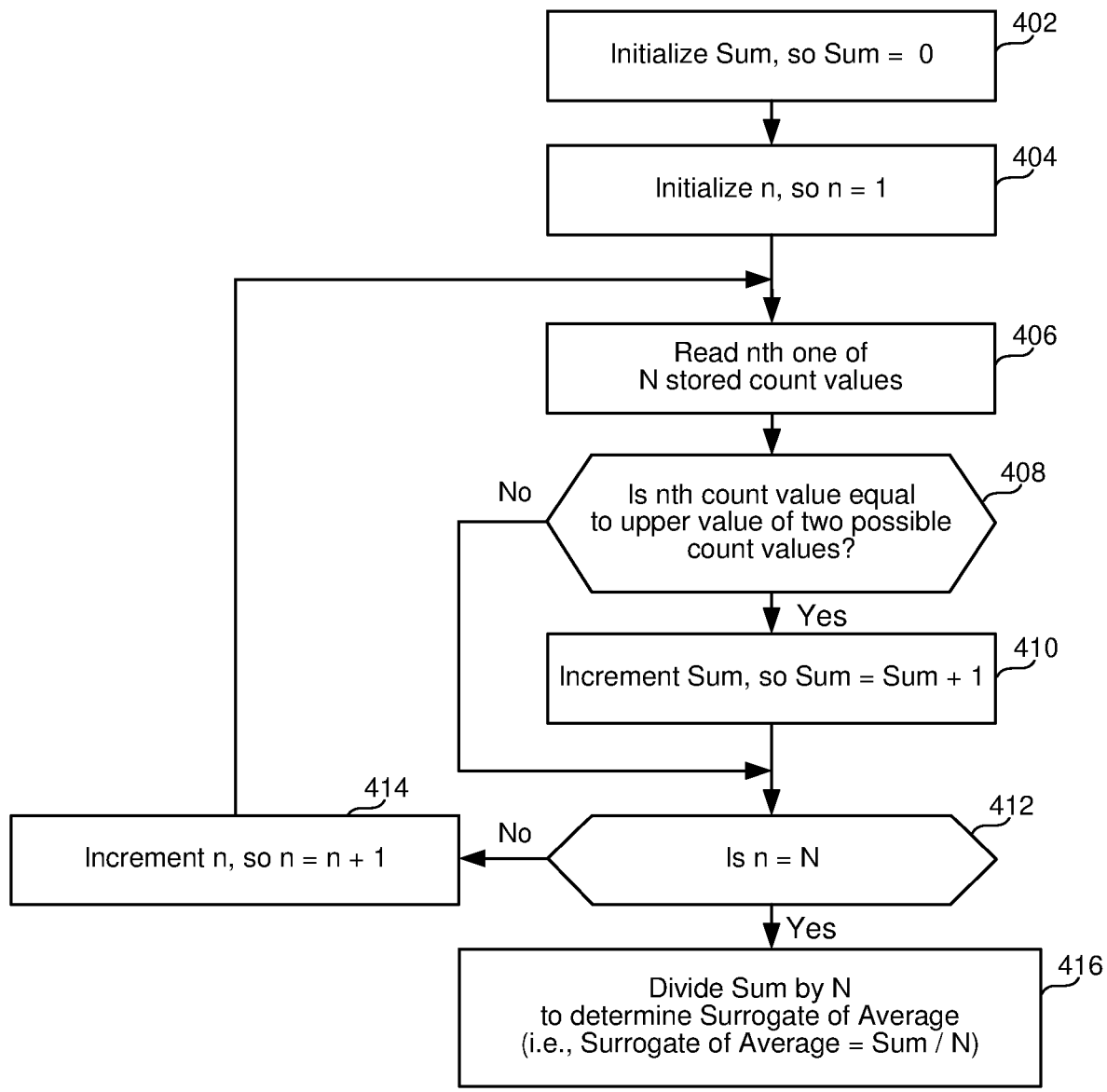
FIG. 4 is a high level flow diagram that is used to describe how a surrogate of an average of N count values can be determined, and used in a method summarized with reference to FIG. 3.
Figure 5:
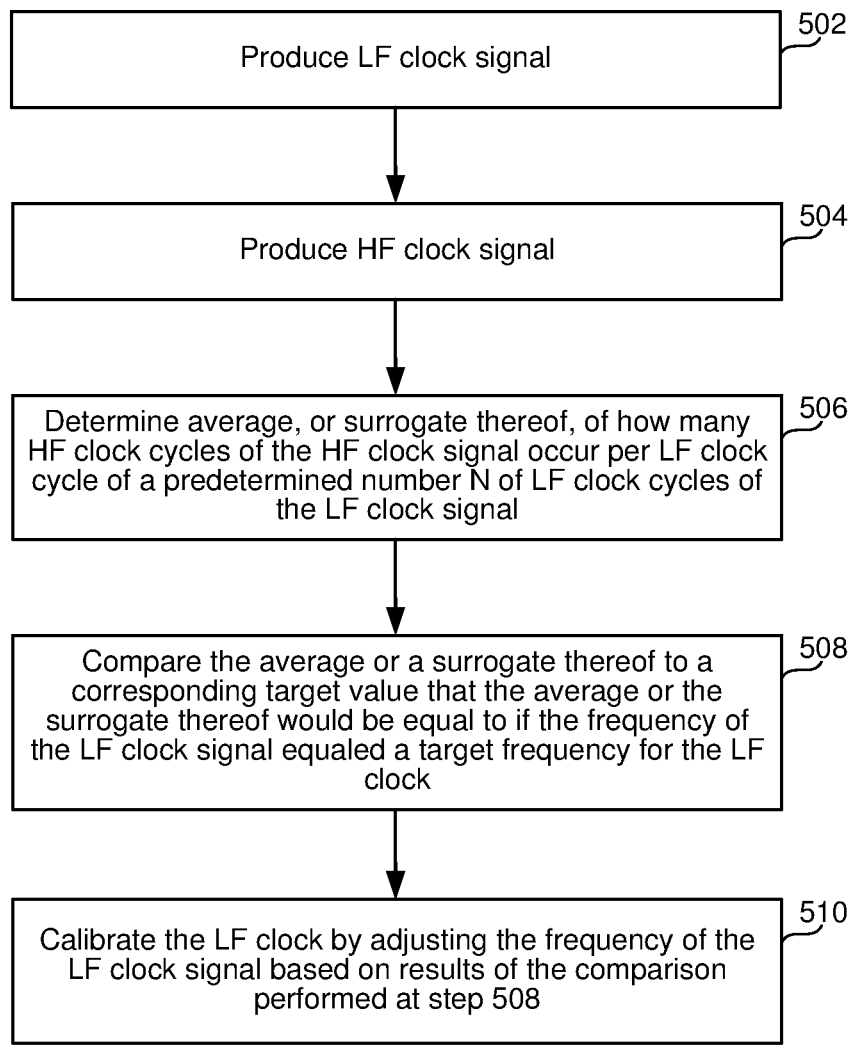
FIG. 5 is a high level flow diagram that is used to more generally summarize methods for calibrating a LF clock signal produced by a LF clock of an IMD, using a HF clock signal produced by a HF clock of the IMD, according to various embodiments of the present technology.

Various methods of the present technology will now be summarized with reference to the high level flow diagrams of FIGS. 3-5. Such methods are for use with an IMD that includes a LF clock (e.g., the LF clock 122) and a HF clock (e.g., the HF clock 124), wherein the HF clock when enabled consumes more power than the LF clock. In certain such embodiments, the HF clock includes a crystal oscillator, and the LF clock includes a non-crystal oscillator, examples of which were discussed above.

Referring to FIG. 3, step 302 involves the LF clock (e.g., 122) producing a LF clock signal, and step 304 involves providing the LF clock signal to an edge detector (e.g., 204). Step 306 involves a HF clock (e.g., 124) producing a HF clock signal that is at least an order of magnitude greater than a frequency of the LF clock signal, and step 308 involves providing the HF clock signal to a counter (e.g., 206). Step 310 involves initializing a value M, so that M=0, wherein M is used to track how many values have been stored in a FIFO register (e.g., 208). Step 312 involves initializing a count value (CNT) of the counter (e.g., 206) so that CNT=0.

At step 314 there is a determination of whether the edge detector (e.g., 204) detected a rising edge of the LF clock signal. When the answer to the determination at step 314 is No, then flow returns to step 314. When the answer to the determination at step 314 is Yes, then flow goes to step 316, and the counter (e.g., 206) is started. Once the counter is started it is incremented in response to each rising edge of the HF clock at step 316.

At step 318 there is a determination of whether the edge detector (e.g., 204) detected the next rising edge of the LF clock signal. When the answer to the determination at step 318 is No, then flow returns to step 318. When the answer to the determination at step 318 is Yes, then flow goes to step 320 and the counter (e.g., 206) is stopped and its count value (CNT) is stored in the FIFO register (e.g., 208). At step 322 the value M is incremented, so that M=M+1.

At step 324 there is a determination of whether M=N. When the answer to the determination at step 324 is No, then flow returns to step 312. When the answer to the determination at step 324 is Yes, then flow goes to step 326. Step 326 involves determining an average of the N count values stored in the FIFO register (e.g., 208), and step 328 involves comparing the average count value to the target count value. As noted above, the target count value is what the average of the N count values would be equal to if the frequency of the LF clock signal equaled a target frequency for the LF clock signal.

At step 330 there is a determination of whether the average count value (i.e., the average of the N count values) is greater than the target count value. If the answer to the determination at step 330 is Yes, then flow goes to step 332. When the average of the N count values is greater than its target value, that is indicative the frequency of the low frequency clock signal being less than the target frequency for the low frequency clock signal. Accordingly, at step 332 the frequency of the low frequency clock signal is increased.

If the answer to the determination at step 330 is No, which means the average count value (i.e., the average of the N count values) is less than or equal to the target count value, then flow goes to step 334. When the average of the N count values is less than its target value, that is indicative the frequency of the low frequency clock signal being greater than the target frequency for the low frequency clock signal. Accordingly, at step 334 the frequency of the low frequency clock signal is decreased. Flow can then return from either step 332 or 334 to step 310. How many times flow returns to step 310 during a calibration procedure depends on the requirements of the LF clock signal, e.g., on how accurate it needs to be. In the above discussion, N is an integer that is at least 2, but is likely at least 10, but may be higher or lower, depending upon the resolution desired.

In alternative embodiments, the edge detector (e.g., 204) can be configured to alternatively detect falling edges rather than rising edges, or if the LF clock cycles has a 50% duty cycle, the edge detector can be configured to detect both rising and falling edges. Other variations are also possible and within the scope of the embodiments described herein. For an example, it can be that no adjustment is made to the LF clock signal if the average count value is equal to the target count value, or within a specified tolerance or range of the target count value.

In the embodiments summarized above, for each LF clock cycle, of N LF clock cycles of the LF clock signal produced by the LF clock, there is a determination of a respective count value indicative of how many HF clock cycles occur during the LF clock cycle, to thereby produce N count values. In alternative embodiments, rather than each of the N count values being indicative of how many HF clock cycles occur during a LF clock cycle, each of the N count values can instead be indicative of how many HF clock cycles occur during a specific portion of LF clock cycle, such as from a rising edge to a falling edge, or from a falling edge to a following rising edge.

In the above described embodiments, the average of the N count values are compared to a target value that the average of the N count values would be equal to if the frequency of the LF clock signal equaled a target frequency for the LF clock signal. In alternative embodiments, rather than determining an actual average of the N count values, a surrogate of the average can instead be determined, and the surrogate can be compared to a corresponding target value that the surrogate of the average of the N count values would be equal to if the frequency of the LF clock signal equaled a target frequency for the LF clock signal. An example of such a surrogate of the average of the N count values is described below with reference to FIG. 4. The results of such comparisons can then be used to either increase or decrease the frequency of the LF clock signal produced by the LF clock.

In certain embodiments, each count value, of the N count values stored in the FIFO register, is either a lower possible count value or an upper possible count value (e.g., has a value of either 488 or 489). Where that is the case, a simplified technique can be used to determine a surrogate of the average of the N count values, rather than an actual average of the N count values. Such an embodiment can involve increasing a sum value by one when the count value is equal to the upper possible value, and not increasing the sum value when the count value is equal to the lower possible value, to thereby produce a total sum value, and then dividing the total sum value by N to thereby produce the surrogate of the average of the N count values. An example implementation of such an embodiment is described below with reference to FIG. 4.

Referring to FIG. 4, step 402 involves initializing the value of the Sum, so that the value of the Sum is equal to 0. Step 404 involves initializing the value of n, so that n=1. Step 406 involves reading the $n^{th}$ one of the N stored count values. Accordingly, the first time step 406 is performed (i.e., when n=1) step 406 involves reading the $1^{st}$ one of the N stored count values; the second time step 406 is performed (i.e., when n=2) step 406 involves reading the $2^{nd}$ of the N stored count values; the third time step 406 is performed (i.e., when n=3) step 406 involves reading the $3^{rd}$ of the N stored count values; . . . and the Nth time step 406 is performed (i.e., when n=N) step 406 involves reading the Nth of the N stored count values.

At step 408 there is a determination of whether the $n^{th}$ count value is equal to the upper value of two possible count values (e.g., is equal to 489, where the two possible count values are 488 and 489). If the answer to the determination at step 408 is Yes, then flow goes to step 410, where the Sum is incremented so that the Sum=Sum+1, and then flow goes to step 412. If the answer to the determination at step 408 is No, then flow goes to step 412, thereby skipping step 410.

At step 412 there is a determination of whether n=N. When the answer to the determination at step 412 is No, then n is incremented at step 414 (so that n=n+1), and then flow returns to step 406. When the answer to the determination at step 412 is Yes, then flow goes to step 416. Step 416 involves determining a surrogate of the average of the N count values by dividing the Sum by N (i.e., the surrogate of the average of the N count values=Sum/N).

The steps described with reference to FIG. 4 can be performed in place of step 326 in FIG. 3. In such an alternative embodiment, step 328 would instead involve comparing the surrogate of the average of the N count values to a corresponding target value that the surrogate of the average of the N count values would be equal to if the frequency of the LF clock signal equaled a target frequency for the LF clock signal; and step 330 would instead involve determining whether the surrogate of the average of the N count values is greater than the corresponding target value that the surrogate of the average of the N count values would be equal to if the frequency of the LF clock signal equaled a target frequency for the LF clock signal.

Referring again to FIG. 4, steps described with reference to FIG. 4 can be performed as part of step 326 to produce an actual average of the N count values, by adding the lower of the two possible count values (e.g., 488, where the two possible count values are 488 and 489) to the results of step 416. Then, there would be no need to modify steps 328 and 330 in FIG. 3. For an example, if the result of step 416 was 0.289, then step 488 can be added to that result to determine that the actual average of the N count values was 488.289.

Another possible surrogate of the average of the N count values is the sum of the N count values, which can be compared to a corresponding target value that the surrogate (i.e., sum of the N count values) would be equal to if the frequency of the LF clock signal equaled a target frequency for the LF clock signal. Other variations are also possible, and within the scope of the embodiments described herein.

In the above described embodiments, for each LF clock cycle, of N LF clock cycles of the LF clock signal produced by the LF clock, a respective count value (indicative of how many HF clock cycles occur during the LF clock cycle) is produced, to thereby produce N count values. Such embodiments can be achieved by counting how many rising edges of the HF clock signal are detected between consecutive rising edges of the LF clock signal, or alternatively, by counting how many falling edges of the HF clock signal are detected between consecutive falling edges of the LF clock signal. Other variations are also possible, and within the scope of the embodiments described herein.

In alternative embodiments, rather than determining how many HF clock cycles occur during a complete LF clock cycle of the LF clock signal, there can be a determinations of how many HF clock cycles occur during a predetermined portion of each LF clock cycle of the LF clock signal. For an example, the predetermined portion of each LF clock cycle can be from a rising edge of the LF clock signal to a following falling edge of the LF clock signal. For another example, the predetermined portion of each LF clock cycle can be from a falling edge of the LF clock signal to a following rising edge of the LF clock signal. More generally, the N count values can be produced by producing a respective count value, for each LF clock cycle or predetermined portion thereof, of N LF clock cycles of the LF clock signal produced by the LF clock, wherein each LF clock cycle or predetermined portion thereof corresponds to one of the following: a time from a rising edge of the LF clock signal to a following rising edge of the LF clock signal; a time from a falling edge of the LF clock signal to a following falling edge of the LF clock signal; a time from a rising edge of the LF clock signal to a following falling edge of the of the LF clock signal; or a time from a falling edge of the LF clock signal to a following rising edge of the LF clock signal.

Referring back to FIG. 3, steps 310 through 332 (or 334), once initiated, can be repeated a predetermined number of times to calibrate the LF clock signal, or can be repeated until the average count value (determined at an instance of step 326) is within some specified tolerance of the target count value. Such steps 310 through 332 (or 334), which are used to calibrate the LF clock signal, can be initiated periodically, e.g., once per hour, once every 8 hours, once per day, once per week, once per month, or the like. Alternatively, or additionally, steps 310 through 332 (or 334), which are used to calibrate the LF clock signal, can be initiated in response to a temperature (sensed by the temperature sensor 111) changing by some specified amount or percentage, since the frequency of a clock signal produced by a non-crystal oscillator tends to drift with changes in temperature. Other variations are also possible, and within the scope of the embodiments described herein.

FIG. 5 is a high level flow diagram that is used to more generally summarize methods for calibrating a LF clock signal produced by a LF clock of an IMD, using a HF clock signal produced by a HF clock of the IMD, according to various embodiments of the present technology. Referring to FIG. 5, step 502 involves a LF clock (e.g., 122) producing a LF clock signal, and step 504 involves a HF clock (e.g., 124) producing a HF clock signal having a frequency that is at least an order of magnitude greater than a frequency of the LF clock signal. As noted above, the HF clock may be selectively enabled and disabled. Still referring to FIG. 5, step 506 involves determining an average, or a surrogate thereof, of how many HF clock cycles of the HF clock signal occur per LF clock cycle of a predetermined number N of LF clock cycles of the LF clock signal. The predetermined number N is an integer that is at least 2, and is likely at least 10, but can be much larger, e.g., 100, or even larger. Step 508 involves comparing the average or a surrogate thereof to a corresponding target value that the average or the surrogate thereof would be equal to if the frequency of the LF clock signal equaled a target frequency for the LF clock, wherein the corresponding target value need not be an integer. Step 510 involves calibrating the LF clock by adjusting the frequency of the LF clock signal based on results of the comparing. As noted above, the HF clock can comprise a crystal oscillator, and the LF clock can comprise a non-crystal oscillator.

In accordance with certain embodiments, determining the average or the surrogate thereof at step 506 involves, for each LF clock cycle or predetermined portion thereof, of the predetermined number N of LF clock cycles of the LF clock signal produced by the LF clock, producing a respective count value indicative of how many HF clock cycles occur during the LF clock cycle or predetermined portion thereof, to thereby produce N count values, wherein each of the N count values is an integer, and determining an average of the N count values or a surrogate thereof. An example of how to determine a surrogate of the average of the N count values was explained above with reference to FIG. 4. In certain embodiments, the N count values are stored in a FIFO register (e.g., 208) of the IMD, and a processor of the IMD determines an average of the N count values stored in the FIFO register, and adjusts the frequency of the LF clock signal based on a comparison of the average to the target count value. Such embodiments can be implemented, e.g., using the clock calibrator 126 shown in FIG. 2A or FIG. 2B.

In accordance with other embodiments, determining the average or the surrogate thereof at step 506 involves, determining an accumulated value that corresponds to how many HF clock cycles of the HF clock signal occur within the predetermined number N of LF clock cycles of the LF clock signal, wherein the accumulated value is an integer, and determining a quotient of the accumulated value divided by the predetermined number N. Such embodiments can be implemented, e.g., using the clock calibrator 126 described above with reference to FIG. 2C. More specifically, determining the accumulated value can include providing the LF clock signal produced by the LF clock to a first counter to thereby produce a first count value that is incremented each LF clock cycle of the LF clock signal, and providing the HF clock signal produced by the HF clock to a second counter to thereby produce a second count value that is incremented each HF clock cycle of the HF clock signal. This can further include comparing the first count value to the predetermined number N to thereby determine when the first count value reaches the predetermined number N, and determining the accumulated value as being equal to the second count value when the first count value reaches the predetermined number N.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed embodiments. For example, it would be possible to combine or separate some of the steps shown in various flow diagrams shown in FIGS. 3, 4 and/or 5. For another example, it is possible to change the boundaries of some of the blocks shown in FIGS. 1 and 2.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are example embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for use with an implantable medical device (IMD) configured to deliver therapy that includes a low frequency clock and a high frequency clock, wherein the high frequency clock when enabled consumes more power than the low frequency clock, the method comprising:
    the low frequency clock producing a low frequency clock signal;
    the high frequency clock producing a high frequency clock signal having a frequency that is at least ten times greater than a frequency of the low frequency clock signal;
    determining an average, or a surrogate thereof, of how many high frequency clock cycles of the high frequency clock signal occur per low frequency clock cycle of a predetermined number N of low frequency clock cycles of the low frequency clock signal,
        wherein the predetermined number N is an integer that is at least 2;
    comparing the average or the surrogate thereof to a corresponding target value that the average or the surrogate thereof would be equal to if the frequency of the low frequency clock signal equaled a target frequency for the low frequency clock,
        wherein the corresponding target value need not be an integer; and
    calibrating the low frequency clock by adjusting the frequency of the low frequency clock signal based on results of the comparing.

2. The method of claim 1, wherein:
    the high frequency clock comprises a crystal oscillator; and
    the low frequency clock comprises a non-crystal oscillator.

3. The method of claim 2, wherein:
    the high frequency clock is part of and/or for use by a radio frequency (RF) communication subsystem of the IMD and is selectively enabled and disabled to thereby reduce an amount of power consumed by the high frequency clock compared to if the high frequency clock was continuously enabled;
    the low frequency clock is part of and/or for use by at least one of a sensor subsystem or a therapy subsystem of the IMD and is continuously enabled; and
    the calibrating the low frequency clock is performed during a period of time that the high frequency clock is enabled.

4. The method of claim 1, wherein the calibrating the low frequency clock, by adjusting the frequency of the low frequency clock signal based on results of the comparing, comprises:
    increasing the frequency of the low frequency clock signal, when the average or the surrogate thereof is greater than the corresponding target value thereof, which is indicative the frequency of the low frequency clock signal being less than the target frequency for the low frequency clock signal; and
    decreasing the frequency of the low frequency clock signal, when the average or the surrogate thereof is less than the corresponding target value thereof, which is indicative the frequency of the low frequency clock signal being greater than the target frequency for the low frequency clock signal.

5. The method of claim 1, wherein the determining the average, or the surrogate thereof, of how many high frequency clock cycles of the high frequency clock signal occur per low frequency clock cycle of the predetermined number N of the low frequency clock cycles of the low frequency clock signal, comprises:
    for each low frequency clock cycle or predetermined portion thereof, of the predetermined number N of low frequency clock cycles of the low frequency clock signal produced by the low frequency clock, producing a respective count value indicative of how many high frequency clock cycles occur during the low frequency clock cycle or predetermined portion thereof, to thereby produce N count values, wherein each of the N count values is an integer; and
    determining an average of the N count values or a surrogate thereof;
    wherein each said low frequency clock cycle or predetermined portion thereof corresponds to one of the following
        a time from a rising edge of the low frequency clock signal to a following rising edge of the low frequency clock signal;
        a time from a falling edge of the low frequency clock signal to a following falling edge of the low frequency clock signal;
        a time from a rising edge of the low frequency clock signal to a following falling edge of the of the low frequency clock signal; or a time from a falling edge of the low frequency clock signal to a following rising edge of the low frequency clock signal.

6. The method of claim 5, wherein:

each said count value, of the N count values, comprises one of a lower possible count value or an upper possible count value; and the determining the average of the N count values or the surrogate thereof comprises determining the surrogate of the average of the N count values by:

for each of the N count values, increasing a sum value by one when the count value is equal to the upper possible value, and not increasing the sum value when the count value is equal to the lower possible value, to thereby produce a total sum value; and dividing the total sum value by N to thereby produce the surrogate of the average of the N count values.

7. The method of claim 5, further comprising:

storing the N count values in a first-in-first-out (FIFO) register of the IMD;

using at least one processor of the IMD to determine, based on the N count values stored in the FIFO register, the average of the N count values or the surrogate thereof; and using the at least one processor to control the calibrating of the low frequency clock.

8. The method of claim 1, wherein the determining the average, or the surrogate thereof, of how many high frequency clock cycles of the high frequency clock signal occur per low frequency clock cycle of the predetermined number N of the low frequency clock cycles of the low frequency clock signal, comprises:

determining an accumulated value that corresponds to how many high frequency clock cycles of the high frequency clock signal occur within the predetermined number N of low frequency clock cycles of the low frequency clock signal, wherein the accumulated value is an integer; and determining a quotient of the accumulated value divided by the predetermined number N.

9. The method of claim 8, wherein the determining the accumulated value comprises:

providing the low frequency clock signal produced by the low frequency clock to a first counter to thereby produce a first count value that is incremented each low frequency clock cycle of the low frequency clock signal;

providing the high frequency clock signal produced by the high frequency clock to a second counter to thereby produce a second count value that is incremented each high frequency clock cycle of the high frequency clock signal;

comparing the first count value to the predetermined number N to thereby determine when the first count value reaches the predetermined number N; and determining the accumulated value as being equal to the second count value when the first count value reaches the predetermined number N.

10. The method of claim 1, wherein the IMD that the method is used with comprises a leadless cardiac pacemaker (LCP) or a subcutaneous implantable cardioverter-defibrillator (SubQ ICD).

11. An implantable medical device (IMD) configured to deliver therapy, comprising:

a low frequency clock configured to produce a low frequency clock signal;

a high frequency clock configured to produce a high frequency clock signal having a frequency that is at least ten times greater than a frequency of the low frequency clock signal, wherein the high frequency clock when enabled consumes more power than the low frequency clock;

a calibration subsystem configured to determine an average, or a surrogate thereof, of how many high frequency clock cycles of the high frequency clock signal occur per low frequency clock cycle of a predetermined number N of low frequency clock cycles of the low frequency clock signal, wherein the predetermined number N is an integer that is at least 2;

compare the average or the surrogate thereof to a corresponding target value that the average or the surrogate thereof would be equal to if the frequency of the low frequency clock signal equaled a target frequency for the low frequency clock, wherein the corresponding target value need not be an integer; and calibrate the low frequency clock by adjusting the frequency of the low frequency clock signal based on results of the comparison.

12. The IMD of claim 11, wherein:

the high frequency clock comprises a crystal oscillator; and the low frequency clock comprises a non-crystal oscillator.

13. The IMD of claim 12, wherein:

the high frequency clock is part of and/or for use by a radio frequency (RF) communication subsystem of the IMD and is selectively enabled and disabled to thereby reduce an amount of power consumed by the high frequency clock compared to if the high frequency clock was continuously enabled;

the low frequency clock is part of and/or for use by at least one of a sensor subsystem or a therapy subsystem of the IMD and is continuously enabled; and the calibration subsystem is configured to calibrate the low frequency clock during a period of time that the high frequency clock is enabled.

14. The IMD of claim 11, wherein the calibration subsystem is configured to:

increase the frequency of the low frequency clock signal, when the average or the surrogate thereof is greater than the corresponding target value thereof, which is indicative the frequency of the low frequency clock signal being less than the target frequency for the low frequency clock signal; and decrease the frequency of the low frequency clock signal, when the average or the surrogate thereof is less than the corresponding target value thereof, which is indicative the frequency of the low frequency clock signal being greater than the target frequency for the low frequency clock signal.

15. The IMD of claim 11, wherein the calibration subsystem is configured to determine the average, or the surrogate thereof, of how many high frequency clock cycles of the high frequency clock signal occur per low frequency clock cycle of the predetermined number N of the low frequency clock cycles of the low frequency clock signal, by:

producing a respective count value indicative of how many high frequency clock cycles occur during the low frequency clock cycle or predetermined portion thereof, for each low frequency clock cycle or predetermined portion thereof, of the predetermined number N of low frequency clock cycles of the low frequency clock signal produced by the low frequency clock, to thereby produce N count values; and determining an average of the N count values or a surrogate thereof.

16. The IMD of claim 15, wherein:

each said count value, of the N count values, comprises one of a lower possible count value or an upper possible count value; and the calibration subsystem is configured to determine the surrogate of the average of the N count values by:

for each of the N count values, increasing a sum value by one when the count value is equal to the upper possible value, and not increasing the sum value when the count value is equal to the lower possible value, to thereby produce a total sum value; and dividing the total sum value by N to thereby produce the surrogate of the average of the N count values.

17. The IMD of claim 11, wherein the IMD comprises a neurostimulator or a pulmonary artery pressure (PAP) sensor.

18. The IMD of claim 15, wherein the calibration subsystem comprises:

a first-in-first-out (FIFO) register configured to store the N count values; and at least one processor configured to determine, based on the N count values stored in the FIFO register, the average of the N count values or the surrogate thereof; and control the calibrating of the low frequency clock based on the average of the N count values or the surrogate thereof.

19. The IMD of claim 11, wherein the calibration subsystem is configured to determine the average, or the surrogate thereof, of how many high frequency clock cycles of the high frequency clock signal occur per low frequency clock cycle of the predetermined number N of the low frequency clock cycles of the low frequency clock signal, by:

determining an accumulated value that corresponds to how many high frequency clock cycles of the high frequency clock signal occur within the predetermined number N of low frequency clock cycles of the low frequency clock signal, wherein the accumulated value is an integer; and determining a quotient of the accumulated value divided by the predetermined number N.

20. The IMD of claim 19, wherein the calibration subsystem comprises:

a first counter that receives the low frequency clock signal produced by the low frequency clock, the first counter configured to produce a first count value that is incremented each low frequency clock cycle of the low frequency clock signal;

a second counter that receives the high frequency clock signal produced by the high frequency clock, the second counter configured to produce a second count value that is incremented each high frequency clock cycle of the high frequency clock signal; and a comparator configured to compare the first count value to the predetermined number N to thereby determine when the first count value reaches the predetermined number N; and wherein the accumulated value, which is divided by the predetermined number N to determine the average, is equal to the second count value when the first count value reaches the predetermined number N.

21. The IMD of claim 11, wherein the IMD comprises a leadless cardiac pacemaker (LCP) or a subcutaneous implantable cardioverter-defibrillator (SubQ ICD).

22. An implantable medical device (IMD) configured to deliver therapy, comprising:

a sensor or therapy subsystem including a low frequency clock, the low frequency clock implemented using a non-crystal oscillator, continuously enabled, and producing a low frequency clock signal;

a radio frequency (RF) communication subsystem including a high frequency clock, the high frequency clock implemented using a crystal oscillator, selectively enabled and disabled, and when enabled consuming more power than the low frequency clock and producing a high frequency clock signal having a frequency that is at least ten times greater than a frequency of the low frequency clock signal;

a first counter configured to produce a first count value that is incremented each low frequency clock cycle of the low frequency clock signal;

a second counter configured to produce a second count value that is incremented each high frequency clock cycle of the high frequency clock signal; and a first comparator configured to compare the first count value to a predetermined number N to thereby determine when the first count value reaches the predetermined number N, wherein N is an integer that is at least 2; and an averager configured to determine an average, or a surrogate thereof, of how many high frequency clock cycles of the high frequency clock signal occur per low frequency clock cycle of the predetermined number N of low frequency clock cycles of the low frequency clock signal;

a second comparator configured to compare the average or the surrogate thereof to a target count value; and a frequency adjuster configured to adjust the frequency of the low frequency clock signal based on an output of the second comparator.

23. The IMD of claim 22, wherein one or more of the first comparator, the second comparator, the averager, and the frequency adjuster is/are implemented using a processor of the IMD.

24. The IMD of claim 22, wherein the averager is configured to determine the average, or the surrogate thereof, of how many high frequency clock cycles of the high frequency clock signal occur per low frequency clock cycle of the predetermined number N of the low frequency clock cycles of the low frequency clock signal, by:

producing a respective count value indicative of how many high frequency clock cycles occur during the low frequency clock cycle or predetermined portion thereof, for each low frequency clock cycle or predetermined portion thereof, of the predetermined number N of low frequency clock cycles of the low frequency clock signal produced by the low frequency clock, to thereby produce N count values; and determining an average of the N count values or a surrogate thereof.

25. The IMD of claim 24, wherein:

each said count value, of the N count values, comprises one of a lower possible count value or an upper possible count value; and the averager is configured to determine the surrogate of the average of the N count values by:
for each of the N count values, increasing a sum value by one when the count value is equal to the upper possible value, and not increasing the sum value when the count value is equal to the lower possible value, to thereby produce a total sum value; and
dividing the total sum value by N to thereby produce the surrogate of the average of the N count values.

* * * * *